(12) United States Patent
Burch

(10) Patent No.: US 12,053,485 B2
(45) Date of Patent: *Aug. 6, 2024

(54) METHODS OF INHIBITING MICROBIAL INFECTIONS USING ZINC-CONTAINING COMPOSITIONS

(71) Applicant: Triumph Pharmaceuticals Inc., St. Louis, MO (US)

(72) Inventor: Andrew Leslie Burch, St. Louis, MO (US)

(73) Assignee: Triumph Pharmaceuticals Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/450,163

(22) Filed: Jun. 24, 2019

(65) Prior Publication Data

US 2019/0388465 A1 Dec. 26, 2019

Related U.S. Application Data

(60) Provisional application No. 62/689,366, filed on Jun. 25, 2018.

(51) Int. Cl.
| | | |
|---|---|---|
| *A61K 31/4425* | (2006.01) | |
| *A23L 33/00* | (2016.01) | |
| *A23L 33/16* | (2016.01) | |
| *A61K 9/00* | (2006.01) | |
| *A61K 9/08* | (2006.01) | |
| *A61K 31/44* | (2006.01) | |
| *A61K 33/00* | (2006.01) | |
| *A61K 33/14* | (2006.01) | |
| *A61K 33/30* | (2006.01) | |
| *A61K 33/40* | (2006.01) | |
| *A61P 31/16* | (2006.01) | |

(52) U.S. Cl.
CPC ............ *A61K 33/30* (2013.01); *A23L 33/16* (2016.08); *A23L 33/40* (2016.08); *A61K 9/0053* (2013.01); *A61K 9/0056* (2013.01); *A61K 9/08* (2013.01); *A61K 31/44* (2013.01); *A61K 31/4425* (2013.01); *A61K 33/00* (2013.01); *A61K 33/14* (2013.01); *A61K 33/40* (2013.01); *A61P 31/16* (2018.01); *A23V 2002/00* (2013.01); *A23V 2200/30* (2013.01); *A23V 2250/152* (2013.01)

(58) Field of Classification Search
CPC ..... A23L 33/16; A23L 33/10; A23V 2002/00; A23V 2200/30; A23V 2250/152; A61K 31/4425; A61K 33/14; A61K 33/30; A61K 33/40; A61K 9/0053; A61K 9/08; A61K 9/006; A61P 31/16; Y02A 50/30
See application file for complete search history.

(56) References Cited

U.S. PATENT DOCUMENTS

| | | |
|---|---|---|
| 4,226,851 A | 10/1980 | Sompayrac |
| 4,692,262 A | 9/1987 | Brown et al. |
| 5,174,990 A | 12/1992 | Douglas |
| 5,310,546 A | 5/1994 | Douglas |
| 5,576,299 A | 11/1996 | Ando et al. |
| 5,958,984 A | 9/1999 | Devillez |
| 6,344,184 B1 | 2/2002 | Rolla |
| 6,409,992 B1 | 6/2002 | Kleinberg et al. |
| 6,423,300 B1 | 7/2002 | Kleinberg et al. |
| 6,723,305 B2 | 4/2004 | DePierro et al. |
| 6,929,790 B2 | 8/2005 | Kleinberg et al. |
| 7,044,466 B2 | 5/2006 | Laibson et al. |
| 7,968,122 B2 | 6/2011 | Chen |
| 8,283,135 B2 | 10/2012 | Doyle et al. |
| 8,853,265 B2 | 10/2014 | Clarot |
| 9,044,466 B2 | 6/2015 | Cohen et al. |
| 9,072,753 B1 | 7/2015 | Brown |
| 9,138,428 B2 | 9/2015 | Cohen et al. |
| 9,480,435 B2 | 11/2016 | Cohen et al. |
| 9,480,635 B2 | 11/2016 | Cohen et al. |
| 10,071,031 B2 | 9/2018 | Cohen et al. |
| 2001/0006624 A1 | 7/2001 | Witt et al. |
| 2002/0150630 A1 | 10/2002 | Brooks et al. |
| 2002/0182267 A1 | 12/2002 | Kleinberg et al. |
| 2003/0165439 A1 | 9/2003 | DePierro et al. |
| 2003/0199430 A1 | 10/2003 | Rosenbloom et al. |
| 2004/0192587 A9 | 9/2004 | Rosenbloom et al. |
| 2005/0142157 A1 | 6/2005 | Alimi |

(Continued)

FOREIGN PATENT DOCUMENTS

| | | |
|---|---|---|
| CN | 101780016 A | 7/2010 |
| CN | 102481357 A | 5/2012 |

(Continued)

OTHER PUBLICATIONS

Ortner ($H_2O_2$-Decontamination Technology, $H_2O_2$ Decontamination Technology.pdf).*

(Continued)

*Primary Examiner* — Jeffrey S Lundgren
*Assistant Examiner* — William Y Lee
(74) *Attorney, Agent, or Firm* — Harness Dickey & Pierce P.L.C.

(57) ABSTRACT

Methods of inhibiting and/or reducing the occurrences and/or duration of microbial infections, such as rhinovirus and influenza infections, are provided herein. The methods comprise delivering an oral composition comprising at least one $E_h$-raising compound and at least one zinc compound to a subject.

12 Claims, 7 Drawing Sheets

(56) References Cited

U.S. PATENT DOCUMENTS

| | | |
|---|---|---|
| 2006/0045855 A1 | 3/2006 | Sasson |
| 2006/0140880 A1 | 6/2006 | Subramanyam et al. |
| 2006/0171907 A1 | 8/2006 | Scott et al. |
| 2007/0292531 A1 | 12/2007 | Clarot et al. |
| 2012/0034280 A1 | 2/2012 | Cohen et al. |
| 2012/0148506 A1 | 6/2012 | Galvan Gonzalez |
| 2013/0164358 A1 | 6/2013 | Cohen et al. |
| 2016/0000826 A1* | 1/2016 | Brown .................. A61K 36/73 424/537 |
| 2016/0008250 A1 | 1/2016 | Cohen et al. |
| 2016/0338922 A1 | 11/2016 | Cohen et al. |
| 2019/0000733 A1 | 1/2019 | Cohen et al. |

FOREIGN PATENT DOCUMENTS

| | | |
|---|---|---|
| CN | 103221031 A | 7/2013 |
| JP | 2001503402 A | 3/2001 |
| JP | 2002538093 A | 11/2002 |
| JP | 2008143910 A | 6/2008 |
| WO | 1998017195 A1 | 4/1998 |
| WO | 2000051559 A1 | 9/2000 |
| WO | 2002002128 A2 | 1/2002 |
| WO | 2005046738 A2 | 5/2005 |
| WO | WO-2005074947 A2 | 8/2005 |
| WO | 2006069210 A2 | 6/2006 |
| WO | 2007134335 A2 | 11/2007 |
| WO | 2009099454 A1 | 8/2009 |
| WO | WO-2009116944 A1 | 9/2009 |
| WO | 2010068444 A2 | 6/2010 |

OTHER PUBLICATIONS

Thomas (Effect of High-Dose Zinc and Ascorbic Acid Supplementation vs Usual Care on Symptom Length and Reduction Among Ambulatory Patients With SARS-CoV-2 Infection, JAMA Network Open. 2021;4(2)).*
Lee (Stop inhaling hydrogen peroxide to try to prevent, treat Covid-19, AAFA says, Oct. 2021, Stop Inhaling Hydrogen Peroxide To Try To Prevent, Treat Covid-19, AAFA Says (forbes.com).*
Mossad et al., "Zinc Gluconate Lozenges for Treating the Common Cold," American College of Physicians, 125(2):81-88 (1996).
Singh et al., "Zinc for the common cold", The Cochrane Library, 2011.
Savi et al., "Antifungal properties of Zinc-compounds against toxigenic fungi and mycotoxin," International Journal of Food Science & Technology, 48: 1834-1840 (2013).
Velthuis et al., Zn2+ Inhibits Coronavirus and Arterivirus RNA Polymerase Activity In Vitro and Zinc Ionophores Block the Replication of These Viruses in Cell Culture,: PLOS Pathogens, 6(11): 1-10 (2010).
Godfrey et al., "A Randomized Clinical Trial on the Treatment of Oral Herpes with Topical Zinc Oxide/Glycine," Alternative Therapies, 7(3): 49-55 (2001).
Edlind et al., "Effects of Cetylpyridinium Chloride Resistance and Treatment on Fluconazole Activity versus Candida albicans," Antimicrobial Agents and Chemotherapy, 49(2): 843-845 (2005).
Sreenivasan et al., "Antimicrobial efficacy of 0×05% cetylpyridinium chloride mouthrinses," Letters in Applied Microbiology, 56: 14-20 (2012).
Geist, F.C., et al., "In Vitro Activity of Zinc Salts against Human Rhinoviruses," Antimichrobial Agents and Chemotherapy (1987), 31(4):622-624.
International Search Report from PCT Application No. PCT/US2019/038746 dated Aug. 29, 2019.
Written Opinion from PCT Application No. PCT/US2019/038746 dated Aug. 29, 2019.
Rolla, G., et al., "The significance of the source of zinc and its anti-VSC effect," Int. Dent J., (2002), 22(52):233-235.
International Preliminary Report on Patentability for PCT Application No. PCT/US2011/046831 dated Feb. 21, 2013.

International Search Report from PCT Application No. PCT/US2011/046831 dated Oct. 23, 2012.
Written Opinion from PCT Application No. PCT/US2011/046831 dated Oct. 23, 2012.
Patent Examination Report from Australian Patent Application No. 2011289661 dated Mar. 14, 2014.
Thrane, P., et al., "A New Mouthrinse Combining Zinc and Chlorhexidine in Low Concentrations Provides Superior Efficacy Against Halitosis Compared to Existing Formulations: A Double-Blind Clinical Study," J. Clin. dent. (2007) 18: 82-86.
Examiner's Search Report and Written Opinion from Singapore Application No. 201300898-2 dated May 15, 2014.
International Preliminary Report on Patentability from PCT Application No. PCT/US2011/046851 dated Feb. 21, 2013.
International Search Report from PCT Application No. PCT/US2011/046851 dated Oct. 19, 2012.
Written Opinion from PCT Application No. PCT/US2011/046851 dated Oct. 19, 2012.
Korean Office Action issued in Korean Patent Application No. 10-2019-7004953 dated Apr. 29, 2019 (6 pages).
International Preliminary Report on Patentability from corresponding PCT Application No. PCT/US2019/038746 dated Dec. 29, 2020.
Te Velthuis, A., et al. (2010), "Zn2+ Inhibits Coronavirus and Arterivirus RNA Polymerase Activity In Vitro and Zinc Ionophores Block the Replication of These Viruses in Cell Culture", PLoS Pathogens, 6(11): 1-10.
Savi, G., et al., (2013), "Anitfungal properties of Zinc-compounds against toxigenic fungi and mycotoxin", International Journal of Food Science & Technology, 48: 1834-1840.
International Search Report from corresponding PCT Application No. PCT/US2019/038746 dated Aug. 29, 2019.
Written Opinion from corresponding PCT Application No. PCT/US2019/038746 dated Aug. 29, 2019.
Geist, F.C., et al., "In Vitro Activity of Zinc Salts against Human Rhinoviruses," Antimicrobial Agents and Chemotherapy, 31(4): 622-624 (1987).
Godfrey, H.R., et al., "A Randomized Clinical Trial on the Treatment of Oral Herpes with Topical Zinc Oxide/Glycine," Alternative Therapies, 7(3): 49-55 (2001).
Mossad, S.B., et al., "Zinc Gluconate Lozenges for Treating the Common Cold," Annals of Internal Medicine, 125(2): 81-88 (1996).
The Cochrane Library, "Zinc for the Common Cold" (2011).
Sreenivasan, P.K., et al., "Antimicrobial efficacy of 0.05% cetylpyridinium chloride mouthrinses," Letters in Applied Microbiology, 56: 14-20 (2012).
Edlind, M.P., et al., "Effects of Cetylpyridinium Chloride Resistance and Treatment on Fluconazole Activity versus Candida albicans," Antimicrobial Agents and Chemotherapy, 49(2): 843-845 (2005).
Butterworth, et al., "Zinc ions inhibit replication of rhinoviruses," Nature, 248: 588-590 (1974).
"New Halo Oral Antiseptic Spray," https://www.globenewswire.com/news-release/2012/08/17/1031372/0/en/New-Halo-Oral-Antiseptic-Spray-Kills-Airborne-Germs-You-Breath-In.html., Published: Aug. 7, 2012.
Office Action from corresponding U.S. Application No. U.S. Appl. No. 17/253,910 dated Feb. 2, 2022.
Thomas, S., et al., "Effect of High-Dose Zinc and Ascorbic Acid Supplementation vs usual Care on Sympton Length and Reduction Among Ambulatory Patients With SARS-CoV-2 Infection," JAMA Network Open, 4(2): 1-10 (2021).
Lee, B.Y., "Stop Inhaling Hydrogen Peroxide To Try To Prevent, Treat Covid-19, AAFA says," Forbes.com, p. 1-7, (2021).
Ortner, "H202-Decontamination Technology," p. 1-4, (2016).
Office Action from corresponding U.S. Appl. No. 16/450,163 dated Jan. 26, 2022.
Nims, R.W., and Zhou, S.S., "Intra-family differences in efficacy of inactivation of small, non-enveloped viruses," Biologicals, 44: 456-462 (2016).
Office Action from corresponding EP Application No. 19827212.2 dated Feb. 15, 2023.

* cited by examiner

| Subject Number | # of Colds | Durations (days) | S1 OUT (oz) | S2 OUT (oz) |
|---|---|---|---|---|
| PT1 | 0 | 0 | 18.6 | 19.1 |
| PT2 | 0 | 0 | 19 | 18.6 |
| PT3 | 0 | 0 | 19 | 18.5 |
| PT4 | 0 | 0 | 19 | 18.6 |
| PT5 | 0 | 0 | 19.3 | 18.5 |
| PT6 | 0 | 0 | 19 | 18.5 |
| PT7 | 0 | 0 | 18.9 | 18.6 |
| PT8 | 1 | 5 | 19.3 | 18.3 |
| PT9 | 2 | 5 | 19.3 | 18.6 |
| PT10 | 0 | 0 | 19.3 | 18.9 |
| PT11 | 0 | 0 | 19.1 | 18.8 |
| PT12 | 0 | 0 | 18.8 | 18.4 |
| PT13 | 0 | 0 | 18.9 | 19 |
| PT14 | 0 | 0 | 18.6 | 18.9 |
| PT15 | 0 | 0 | 18.4 | 19.2 |
| PT16 | 0 | 0 | 18.4 | 19 |
| PT17 | 0 | 0 | 18.7 | 19.2 |
| PT18 | 0 | 0 | 18.5 | 18.9 |
| PT19 | 0 | 0 | 17.8 | 18.9 |
| PT20 | 0 | 0 | 18.8 | 19.1 |
| PT21 | 0 | 0 | 18.5 | 19 |
| PT22 | 0 | 0 | 18.4 | 18.8 |
| PT23 | 0 | 0 | 18.5 | 19 |
| PT24 | 0 | 0 | 18.8 | 19 |
| PT25 | 0 | 0 | 18.4 | 19.2 |
| PT26 | 0 | 0 | 18.4 | 19.2 |
| PT27 | 0 | 0 | 18.7 | 18.9 |
| PT28 | 1 | 7 | 18.5 | 19.2 |
| PT29 | 0 | 0 | 18.5 | 18.9 |
| PT30 | 0 | 0 | 18.6 | 19 |
| PT31 | 0 | 0 | 18.4 | 19 |
| PT32 | 0 | 0 | 18.4 | 19.2 |
| PT33 | 0 | 0 | 18.7 | 18.9 |
| PT34 | 0 | 0 | 18.4 | 18.8 |
| PT35 | 0 | 0 | 18.3 | 19 |
| PT36 | 0 | 0 | 18.5 | 19.2 |
| PT37 | 0 | 0 | 19.1 | 19.3 |
| PT38 | 0 | 0 | 19 | 19.3 |
| PT39 | 0 | 0 | 18.9 | 18.9 |
| PT40 | 0 | 0 | 19.1 | 18.8 |
| PT41 | 0 | 0 | 18.7 | 18.9 |
| PT42 | 0 | 0 | 19 | 19.2 |
| PT43 | 0 | 0 | 18.9 | 19.3 |
| PT44 | 0 | 0 | 18.8 | 19.2 |
| PT45 | 0 | 0 | 18.9 | 19.1 |
| PT46 | 0 | 0 | 18.4 | 19.3 |
| PT47 | 0 | 0 | 18.7 | 19.2 |

FIG. 1

| Subject Number | # of Colds | Durations | S1 IN (oz) | S2 IN (oz) | S1 OUT (oz) | S2 OUT (oz) | S1 Used (oz) | S2 Used (oz) | Exp use S1 (oz) | Exp use S2 (oz) | S1 % Compliant | S2 % Compliant |
|---|---|---|---|---|---|---|---|---|---|---|---|---|
| PT1 | 0 | 0 | 4 | 6.6 | 18.2 | 19.1 | 14.6 | 12.5 | 16 | 16 | 91% | 78% |
| PT2 | 0 | 0 | 1.5 | 1.4 | 18.9 | 16.5 | 17.5 | 17.2 | 16 | 16 | 109% | 108% |
| PT3 | 0 | 0 | 3.8 | 3.6 | 19 | 18.8 | 15.2 | 14.9 | 16 | 16 | 95% | 93% |
| PT4 | 1 | 12 | 6.4 | 5.3 | 19.1 | 18.6 | 12.6 | 13.3 | 16 | 16 | 79% | 83% |
| PT5 | 1 | 3 | 1.4 | 1.4 | 19 | 18.8 | 17.9 | 17.1 | 16 | 16 | 112% | 107% |
| PT6 | 0 | 0 | 1.5 | 2.7 | 18.9 | 18.6 | 17.5 | 15.8 | 16 | 16 | 109% | 99% |
| PT7 | 0 | 0 | 9.6 | 8.2 | 18.9 | 18.6 | 9.3 | 10.4 | 16 | 16 | 58% | 65% |
| PT8 | 0 | 0 | 6.5 | 5 | 19 | 18.5 | 12.8 | 13.3 | 16 | 16 | 80% | 83% |
| PT9 | 0 | 0 | 1.4 | 1.5 | 18.9 | 18.8 | 17.9 | 17.1 | 16 | 16 | 112% | 107% |
| PT10 | 0 | 0 | 2.3 | 1.8 | 19.3 | 18.6 | 17 | 17.1 | 16 | 16 | 106% | 107% |
| PT11 | 1 | 10 | 5.5 | 4.2 | 19 | 18.8 | 13.6 | 14.6 | 16 | 16 | 85% | 91% |
| PT12 | 0 | 0 | 8.7 | 7.9 | 19 | 18.5 | 10.1 | 10.5 | 16 | 16 | 63% | 66% |
| PT13 | 0 | 0 | 2.5 | 2.8 | 18.7 | 19.1 | 16.4 | 16.2 | 16 | 16 | 103% | 101% |
| PT14 | 0 | 0 | 4.7 | 5.5 | 18.4 | 19 | 13.9 | 13.4 | 16 | 16 | 87% | 84% |
| PT15 | 0 | 0 | 3 | 3.6 | 18.4 | 18.8 | 15.4 | 15.6 | 16 | 16 | 96% | 98% |
| PT16 | 0 | 0 | 3.1 | 3.3 | 18.4 | 18.9 | 15.3 | 15.7 | 16 | 16 | 96% | 98% |
| PT17 | 0 | 0 | 2.7 | 3 | 18.7 | 19.2 | 16 | 16.2 | 16 | 16 | 100% | 101% |
| PT18 | 0 | 0 | 1.4 | 1.4 | 18.5 | 17.6 | 17.1 | 17.5 | 16 | 16 | 107% | 109% |
| PT19 | 0 | 0 | 2.6 | 2.8 | 18.7 | 19.2 | 15.2 | 16.1 | 16 | 16 | 95% | 101% |
| PT20 | 0 | 0 | 5.1 | 5.8 | 18.5 | 18.9 | 13.7 | 13.3 | 16 | 16 | 86% | 83% |
| PT21 | 0 | 0 | 5.2 | 5.9 | 18.4 | 18.9 | 13.3 | 13.1 | 16 | 16 | 83% | 82% |
| PT22 | 1 | 1 | 2.9 | 3 | 18.4 | 19 | 15.5 | 15.8 | 16 | 16 | 97% | 99% |
| PT23 | 1 | 3 | 3.1 | 2.9 | 18.7 | 19 | 15.4 | 16.1 | 16 | 16 | 96% | 101% |
| PT24 | 0 | 0 | 4.6 | 5.7 | 18.5 | 18.8 | 14.2 | 13.3 | 16 | 16 | 89% | 83% |
| PT25 | 1 | 1 | 3.4 | 4.3 | 18.4 | 19 | 15 | 14.9 | 16 | 16 | 94% | 93% |

FIG. 2

| Subject Number | # of Colds | Durations | S1 IN (oz) | S2 IN (oz) | S1 OUT (oz) | S2 OUT (oz) | S1 Used (oz) | S2 Used (oz) | Exp use S1 (oz) | Exp use S2 (oz) | S1 % Compliant | S2 % Compliant |
|---|---|---|---|---|---|---|---|---|---|---|---|---|
| PT26 | 0 | 0 | 5.2 | 5.3 | 18.4 | 19.2 | 13.2 | 13.9 | 16 | 16 | 83% | 87% |
| PT27 | 0 | 0 | 4.9 | 6.1 | 18.4 | 19.2 | 13.8 | 12.8 | 16 | 16 | 86% | 80% |
| PT28 | 0 | 0 | 2.9 | 3.1 | 18.5 | 19.2 | 15.6 | 16.1 | 16 | 16 | 98% | 101% |
| PT29 | 0 | 0 | 5.6 | 5.1 | 18.4 | 18.9 | 12.9 | 13.8 | 16 | 16 | 81% | 86% |
| PT30 | 0 | 0 | 4.8 | 5.1 | 18.7 | 18.9 | 13.8 | 13.9 | 16 | 16 | 86% | 87% |
| PT31 | 1 | 4 | 9.2 | 9.5 | 18.6 | 19.1 | 9.2 | 9.5 | 16 | 16 | 58% | 59% |
| PT32 | 0 | 0 | 4.7 | 4.8 | 18.7 | 19.2 | 13.7 | 14.4 | 16 | 16 | 86% | 90% |
| PT33 | 0 | 0 | 5.4 | 5.3 | 18.7 | 19.2 | 13.3 | 13.6 | 16 | 16 | 83% | 85% |
| PT34 | 0 | 0 | 2.6 | 2.4 | 18.7 | 18.9 | 15.8 | 16.4 | 16 | 16 | 99% | 103% |
| PT35 | 0 | 0 | 2.6 | 4.9 | 18.5 | 18.8 | 15.7 | 14.1 | 16 | 16 | 98% | 88% |
| PT36 | 0 | 0 | 3.8 | 3.5 | 18.4 | 19 | 14.7 | 15.7 | 16 | 16 | 92% | 98% |
| PT37 | 0 | 0 | 19.1 | 19.3 | 19 | 19.3 | 0 | 0 | 16 | 16 | 0% | 0% |
| PT38 | 0 | 0 | 19 | 19.3 | 18.8 | 19.2 | 0 | 0 | 16 | 16 | 0% | 0% |
| PT39 | 1 | 4 | 13.1 | 12.9 | 18.3 | 19.1 | 5.8 | 6 | 16 | 16 | 36% | 38% |
| PT40 | 0 | 0 | 19.1 | 18.8 | 18.5 | 18.9 | 0 | 0 | 16 | 16 | 0% | 0% |
| PT41 | 0 | 0 | 18.7 | 18.9 | 18.9 | 19 | 0 | 0 | 16 | 16 | 0% | 0% |
| PT42 | 0 | 0 | 19 | 19.2 | 18.8 | 19.2 | 0 | 0 | 16 | 16 | 0% | 0% |
| PT43 | 0 | 0 | 18.9 | 19.3 | 19 | 19.1 | 0 | 0 | 16 | 16 | 0% | 0% |
| PT44 | 0 | 0 | 18.8 | 19.2 | 18.7 | 19 | 0 | 0 | 16 | 16 | 0% | 0% |
| PT45 | 0 | 0 | 18.9 | 19.1 | 18.7 | 18.9 | 0 | 0 | 16 | 16 | 0% | 0% |
| PT46 | 0 | 0 | 4.2 | 4.5 | 18.8 | 19.3 | 14.2 | 14.8 | 16 | 16 | 89% | 93% |
| PT47 | 1 | 1 | 18.3 | 18.9 | 18.7 | 19 | 0.4 | 0.3 | 16 | 16 | 2% | 2% |

FIG. 2 (cont.)

| Subject Number | # of Colds | Durations | S1 IN | S2 IN | S1 OUT | S2 OUT | S1 Used | S2 Used | Exp use S1 (oz) | Exp use S2 (oz) | S1 % Compliant | S2 % Compliant |
|---|---|---|---|---|---|---|---|---|---|---|---|---|
| PT1 | 1 | 8 | 5.7 | 7.3 | 18.6 | 19.1 | 12.5 | 11.8 | 16 | 16 | 78% | 74% |
| PT2 | 0 | 0 | 1.5 | 1.4 | 19 | 18.8 | 17.4 | 15.1 | 16 | 16 | 109% | 94% |
| PT3 | 0 | 0 | 1.4 | 1.4 | 19 | 16.8 | 17.6 | 17.4 | 16 | 16 | 110% | 109% |
| PT4 | 0 | 0 | 4.3 | 4.2 | 19.3 | 18.4 | 14.8 | 14.4 | 16 | 16 | 93% | 90% |
| PT5 | 1 | 2 | 1.4 | 1.5 | 19.2 | 18.9 | 17.6 | 17.3 | 16 | 16 | 110% | 108% |
| PT6 | 0 | 0 | 1.5 | 1.5 | 19.3 | 18.6 | 17.4 | 17.1 | 16 | 16 | 109% | 107% |
| PT7 | 0 | 0 | 11.3 | 10.8 | 19.3 | 18.8 | 7.6 | 7.8 | 16 | 16 | 48% | 49% |
| PT8 | 1 | 5 | 8 | 7.7 | 19 | 18.5 | 11 | 10.8 | 16 | 16 | 69% | 68% |
| PT9 | 0 | 0 | 1.5 | 1.4 | 19.3 | 18.8 | 17.4 | 17.4 | 16 | 16 | 109% | 109% |
| PT10 | 0 | 0 | 1.8 | 1.4 | 18.9 | 18.5 | 17.5 | 17.2 | 16 | 16 | 109% | 108% |
| PT11 | 1 | 5 | 1.5 | 2.2 | 19 | 18.5 | 17.5 | 16.6 | 16 | 16 | 109% | 104% |
| PT12 | 0 | 0 | 1.5 | 1.4 | 19.1 | 18.5 | 17.5 | 17.1 | 16 | 16 | 109% | 107% |
| PT13 | 0 | 0 | 1.8 | 2 | 19 | 19.1 | 16.9 | 17.1 | 16 | 16 | 106% | 107% |
| PT14 | 0 | 0 | 4.6 | 5.9 | 18.7 | 18.9 | 13.8 | 13.1 | 16 | 16 | 86% | 82% |
| PT15 | 0 | 0 | 3.3 | 4.4 | 18.4 | 19.2 | 15.1 | 14.4 | 16 | 16 | 94% | 90% |
| PT16 | 0 | 0 | 6.4 | 5.2 | 18.4 | 18.9 | 12 | 13.7 | 16 | 16 | 75% | 86% |
| PT17 | 0 | 0 | 2.8 | 2.9 | 18.6 | 18.9 | 15.9 | 16.3 | 16 | 16 | 99% | 102% |
| PT18 | 0 | 0 | 1.3 | 1.4 | 18.9 | 18.9 | 17.2 | 16.2 | 16 | 16 | 108% | 101% |
| PT19 | 0 | 0 | 3.8 | 2.9 | 19 | 19.3 | 14.9 | 16.3 | 16 | 16 | 93% | 102% |
| PT20 | 1 | 10 | 1.6 | 1.5 | 18.3 | 19.2 | 16.9 | 17.4 | 16 | 16 | 106% | 109% |
| PT21 | 0 | 0 | 5.7 | 6.2 | 18.6 | 18.8 | 12.7 | 12.7 | 16 | 16 | 79% | 79% |
| PT22 | 0 | 0 | 2.6 | 2.9 | 18.4 | 19.2 | 15.8 | 16.1 | 16 | 16 | 99% | 101% |
| PT23 | 0 | 0 | 2.7 | 3 | 18.7 | 19.2 | 16 | 16 | 16 | 16 | 100% | 100% |
| PT24 | 0 | 0 | 4.9 | 6.5 | 18.7 | 19 | 13.6 | 12.3 | 16 | 16 | 85% | 77% |
| PT25 | 0 | 0 | 2.2 | 3.7 | 18.5 | 18.9 | 16.2 | 15.3 | 16 | 16 | 101% | 96% |

FIG. 3

| Subject Number | # of Colds | Durations | S1 IN | S2 IN | S1 OUT | S2 OUT | S1 Used | S2 Used | Exp use S1 (oz) | Exp use S2 (oz) | S1 % Compliant | S2 % Compliant |
|---|---|---|---|---|---|---|---|---|---|---|---|---|
| PT26 | 0 | 0 | 5 | 5.4 | 18.5 | 18.8 | 13.4 | 13.8 | 16 | 16 | 84% | 86% |
| PT27 | 1 | 10 | 2 | 4.2 | 18.5 | 19.2 | 16.4 | 15 | 16 | 16 | 103% | 94% |
| PT28 | 1 | 5 | 2 | 2.5 | 18.4 | 18.9 | 16.5 | 16.7 | 16 | 16 | 103% | 104% |
| PT29 | 0 | 0 | 5.3 | 5.4 | 18.4 | 18.8 | 13.1 | 13.5 | 16 | 16 | 82% | 84% |
| PT30 | 0 | 0 | 4.2 | 4.4 | 18.4 | 19 | 14.5 | 14.5 | 16 | 16 | 91% | 91% |
| PT31 | 0 | 0 | 5.6 | 6 | 18.5 | 19 | 13 | 13.1 | 16 | 16 | 81% | 82% |
| PT32 | 0 | 0 | 4.1 | 4.4 | 18.4 | 18.8 | 14.6 | 14.8 | 16 | 16 | 91% | 93% |
| PT33 | 0 | 0 | 3.6 | 4.8 | 18.5 | 18.9 | 15.1 | 14.4 | 16 | 16 | 94% | 90% |
| PT34 | 0 | 0 | 2.1 | 2.2 | 18.5 | 18.8 | 16.6 | 16.7 | 16 | 16 | 104% | 104% |
| PT35 | 0 | 0 | 5.1 | 5.9 | 18.5 | 19 | 13.4 | 12.9 | 16 | 16 | 84% | 81% |
| PT36 | 0 | 0 | 1.4 | 1.5 | 18.4 | 18.8 | 17 | 17.5 | 16 | 16 | 106% | 109% |
| PT37 | 0 | 0 | 19 | 19.3 | 18.5 | 18.9 | 0 | 0 | 16 | 16 | 0% | 0% |
| PT38 | 0 | 0 | 18.8 | 19.2 | 18.5 | 18.7 | 0 | 0 | 16 | 16 | 0% | 0% |
| PT39 | 1 | 4 | 15 | 16 | 18.3 | 19.1 | 3.3 | 3.1 | 16 | 16 | 21% | 19% |
| PT40 | 0 | 0 | 18.5 | 18.9 | 15.8 | 18.8 | 0 | 0 | 16 | 16 | 0% | 0% |
| PT41 | 0 | 0 | 18.9 | 19 | 18.4 | 18.8 | 0 | 0 | 16 | 16 | 0% | 0% |
| PT42 | 1 | 2 | 15 | 14.4 | 18.6 | 18.9 | 3.8 | 4.8 | 16 | 16 | 24% | 30% |
| PT43 | 0 | 0 | 19 | 19.3 | 18.7 | 18.9 | 0 | -0.2 | 16 | 16 | 0% | -1% |
| PT44 | 0 | 0 | 18.7 | 19 | 18.9 | 18.4 | 0 | 0 | 16 | 16 | 0% | 0% |
| PT45 | 0 | 0 | 18.7 | 18.9 | 18.5 | 18.8 | 0 | 0 | 16 | 16 | 0% | 0% |
| PT46 | 0 | 0 | 4.4 | 4.5 | 18.7 | 19.1 | 14.4 | 14.8 | 16 | 16 | 90% | 93% |
| PT47 | 0 | 0 | 18.7 | 19 | 18.8 | 19.3 | 0 | 0 | 16 | 16 | 0% | 0% |

FIG. 3 (cont.)

| Subject Number | # of Colds | Durations | S1 IN | S2 IN | S1 Used | S2 Used | Exp use S1 (oz) | Exp use S2 (oz) | S1 % Compliant | S2 % Compliant |
|---|---|---|---|---|---|---|---|---|---|---|
| PT1 | 0 | 0 | 7.5 | 8.3 | 11.1 | 10.8 | 16 | 16 | 69% | 68% |
| PT2 | 0 | 0 | 1.5 | 1.4 | 17.5 | 17.4 | 16 | 16 | 109% | 109% |
| PT3 | 0 | 0 | 1.5 | 1.5 | 17.5 | 15.3 | 16 | 16 | 109% | 96% |
| PT4 | 0 | 0 | 7.6 | 6.8 | 11.7 | 11.6 | 16 | 16 | 73% | 73% |
| PT5 | 0 | 0 | 1.4 | 1.4 | 17.8 | 17.5 | 16 | 16 | 111% | 109% |
| PT6 | 0 | 0 | 1.8 | 2 | 17.5 | 16.6 | 16 | 16 | 109% | 104% |
| PT7 | 0 | 0 | 10.4 | 10.8 | 8.9 | 8 | 16 | 16 | 56% | 50% |
| PT8 | 0 | 0 | 9.9 | 8 | 9.1 | 10.5 | 16 | 16 | 57% | 66% |
| PT9 | 1 | 5 | 1.4 | 1.4 | 17.9 | 17.4 | 16 | 16 | 112% | 109% |
| PT10 | 0 | 0 | 1.5 | 1.8 | 17.4 | 16.7 | 16 | 16 | 109% | 104% |
| PT11 | 0 | 0 | 1.8 | 2 | 17.2 | 16.5 | 16 | 16 | 108% | 103% |
| PT12 | 0 | 0 | 1.6 | 1.9 | 17.5 | 16.6 | 16 | 16 | 109% | 104% |
| PT13 | 0 | 0 | 2 | 2 | 17 | 17.1 | 16 | 16 | 106% | 107% |
| PT14 | 0 | 0 | 4.2 | 4.4 | 14.5 | 14.5 | 16 | 16 | 91% | 91% |
| PT15 | 0 | 0 | 3.2 | 3.7 | 15.2 | 15.5 | 16 | 16 | 95% | 97% |
| PT16 | 0 | 0 | 3.3 | 2.8 | 15.1 | 16.1 | 16 | 16 | 94% | 101% |
| PT17 | 0 | 0 | 2.9 | 3.1 | 15.7 | 15.8 | 16 | 16 | 98% | 99% |
| PT18 | 0 | 0 | 1.4 | 1.5 | 17.5 | 17.4 | 16 | 16 | 109% | 109% |
| PT19 | 0 | 0 | 2.9 | 3.2 | 16.1 | 16.1 | 16 | 16 | 101% | 101% |
| PT20 | 0 | 0 | 2.4 | 2.5 | 15.9 | 16.7 | 16 | 16 | 99% | 104% |
| PT21 | 0 | 0 | 3.1 | 2.8 | 15.5 | 16 | 16 | 16 | 97% | 100% |
| PT22 | 0 | 0 | 1.5 | 1.6 | 16.9 | 17.6 | 16 | 16 | 106% | 110% |
| PT23 | 0 | 0 | 1.9 | 2 | 16.8 | 17.2 | 16 | 16 | 105% | 108% |
| PT24 | 0 | 0 | 3.5 | 4.5 | 15.2 | 14.5 | 16 | 16 | 95% | 91% |
| PT25 | 0 | 0 | 3.6 | 4 | 14.9 | 14.9 | 16 | 16 | 93% | 93% |

FIG. 4

| Subject Number | # of Colds | Durations | S1 IN | S2 IN | S1 Used | S2 Used | Exp use S1 (oz) | Exp use S2 (oz) | S1 % Compliant | S2 % Compliant |
|---|---|---|---|---|---|---|---|---|---|---|
| PT26 | 0 | 0 | 5.3 | 5.6 | 13.2 | 13.2 | 16 | 16 | 83% | 83% |
| PT27 | 0 | 0 | 2.1 | 3 | 16.4 | 16.2 | 16 | 16 | 103% | 101% |
| PT28 | 0 | 0 | 2.2 | 2.8 | 16.2 | 16.1 | 16 | 16 | 101% | 101% |
| PT29 | 0 | 0 | 4.9 | 5.2 | 13.5 | 13.6 | 16 | 16 | 84% | 85% |
| PT30 | 0 | 0 | 4.6 | 4.7 | 13.8 | 14.3 | 16 | 16 | 86% | 89% |
| PT31 | 0 | 0 | 5.3 | 5.8 | 13.2 | 13.2 | 16 | 16 | 83% | 83% |
| PT32 | 0 | 0 | 4.2 | 4.3 | 14.2 | 14.5 | 16 | 16 | 89% | 91% |
| PT33 | 0 | 0 | 3.8 | 4.3 | 14.7 | 14.6 | 16 | 16 | 92% | 91% |
| PT34 | 0 | 0 | 3.2 | 3.3 | 15.3 | 15.5 | 16 | 16 | 96% | 97% |
| PT35 | 0 | 0 | 4.8 | 5 | 13.7 | 14 | 16 | 16 | 86% | 88% |
| PT36 | 0 | 0 | 1.6 | 1.7 | 16.8 | 17.1 | 16 | 16 | 105% | 107% |
| PT37 | 1 | 3 | 15.5 | 16.6 | 3 | 2.3 | 16 | 16 | 19% | 14% |
| PT38 | 0 | 0 | 18.5 | 18.7 | 0 | 0 | 16 | 16 | 0% | 0% |
| PT39 | 1 | 4 | 15.7 | 16.7 | 2.6 | 2.4 | 16 | 16 | 16% | 15% |
| PT40 | 1 | 3 | 8.9 | 10.1 | 6.9 | 8.7 | 16 | 16 | 43% | 54% |
| PT41 | 0 | 0 | 18.4 | 18.8 | 0 | 0 | 16 | 16 | 0% | 0% |
| PT42 | 0 | 0 | 18.6 | 18.9 | 0 | 0 | 16 | 16 | 0% | 0% |
| PT43 | 0 | 0 | 18.7 | 18.9 | 0 | 0 | 16 | 16 | 0% | 0% |
| PT44 | 0 | 0 | 18.9 | 18.4 | 0 | 0 | 16 | 16 | 0% | 0% |
| PT45 | 0 | 0 | 18.5 | 18.8 | 0 | 0 | 16 | 16 | 0% | 0% |
| PT46 | 0 | 0 | 4.9 | 5.1 | 13.8 | 14 | 16 | 16 | 86% | 88% |
| PT47 | 0 | 0 | 18.8 | 19.3 | 0 | 0 | 16 | 16 | 0% | 0% |

FIG. 4 (cont.)

METHODS OF INHIBITING MICROBIAL INFECTIONS USING ZINC-CONTAINING COMPOSITIONS

CROSS-REFERENCE TO RELATED APPLICATIONS

This patent application claims the benefit of U.S. Provisional Patent Application No. 62/689,366 filed on 25 Jun. 2018. The entire contents of U.S. 62/689,366 is hereby incorporated by reference.

FIELD

The present disclosure relates generally to methods for inhibiting and/or reducing the occurrence and/or duration of a microbial infection, such as a rhinovirus or influenza infection. The methods comprise delivering an oral composition comprising at least one Eh-raising compound and at least one zinc compound to a subject.

BACKGROUND

The body hosts a diverse array of microflora, including bacteria, fungi, and viruses. Most of these microbes reside at body surfaces which are in direct contact with the environment, such as the skin, respiratory tract and mucosal surfaces, including the oral cavity (Duerkop, et al., Nature Immunology. 2013). The microbes can cause an infection, for example, when the oral surface is compromised, allowing a microbe to enter the body, or when there is a shift in the relative populations of the various microbes which reside in the oral cavity.

Microbes may induce many oral diseases, and the oral cavity can be a point of entry for various pathogens. New methods are needed to reduce the opportunity for microbes to infect a subject or reduce the duration of an infection. Such methods would promote the health and well-being of the subject.

SUMMARY

It has been found that oral compositions comprising a first component comprising an Eh-raising compound and a second component comprising at least one zinc compound are effective for inhibiting a microbial infection. Therefore, methods for inhibiting a microbial infection, reducing the occurrence or number of microbial infections suffered by a subject, and/or shortening the duration of a microbial infection are provided herein. The methods may comprise delivering an oral composition as described herein to an oral cavity in a subject. The subject may be a human or a non-human animal. Systems and kits containing an oral composition as described herein are also provided.

Other embodiments, including particular aspects of the embodiments summarized above, will be evident from the following detailed description. The description and specific examples in this summary are intended for purposes of illustration only and are not intended to limit the scope of the present disclosure.

BRIEF DESCRIPTION OF THE DRAWINGS

The figures described herein are for illustrative purposes only of selected embodiments and not all possible implementations. The figures are not intended to limit the scope of the present disclosure.

FIG. 1 is a table displaying results of the study conducted in Example 37 herein on visit 2.

FIG. 2 is a table displaying results of the study conducted in Example 37 on visit 3.

FIG. 3 is a table displaying results of the study conducted in Example 37 on visit 4.

FIG. 4 is a table displaying results of the study conducted in Example 37 on visit 5.

DETAILED DESCRIPTION

In various aspects of the invention, oral compositions comprising a first component comprising an Eh-raising compound and a second component comprising a zinc compound are provided. Also provided are methods for inhibiting a microbial infection, reducing the number or occurrence of microbial infections suffered by a subject, and shortening the duration of a microbial infection comprising administration of said oral composition to the oral cavity of the subject.

I. Definitions

As used herein, the term "oral composition" is intended to include various embodiments of compositions that are useful for all aspects of oral hygiene including, but not limited to, inhibiting a microbial infection, reducing the number of microbial infections in an individual, shortening the duration of a microbial infection, preventing and/or treating oral disease, maintaining oral health, reducing or eliminating bad breath (oral malodor), whitening teeth, preventing gum deterioration, and/or preventing tooth decay. More particularly, the oral composition facilitates preventing oral microbes from reducing the oxidation-reduction potential (Eh) of an oral cavity and, at the same time, increasing the existing oxidation-reduction potential to a level, wherein an oral environment is created that is not conducive to microbes in the oral cavity. Further, the oral composition can be used for inhibiting the formation of sulfur-containing anions, reducing gingivitis, reducing the formation of dental caries, reducing canker sores, inhibiting plaque formation, and/or reducing plaque and tartar (calculus) formation.

As used herein, the term "Eh-raising" is defined as a compound capable of directly or indirectly raising the Eh of the oral cavity.

As used herein, the term "zinc compound" is defined as a compound capable of providing freely available zinc ions. Without being bound by theory, it is believed that the freely available zinc ions are capable of inhibiting a decrease of the Eh in the oral cavity. Unbound zinc ions are freely available, and therefore have a greater reaction with Eh-lowering enzymes within the oral cavity than bound zinc ions. Moreover, zinc ions have been shown to possess antimicrobial properties, as it disrupts the cellular machinery of the microbe. These freely available zinc ions may also inhibit the breakdown of cysteine or cystine from saliva, mucosal tissues, and/or foods by oral bacteria. As such, oral bacteria are prevented from lowering the existing Eh within the oral cavity.

As used herein, the term "microbe" or "microbial" is defined as a microorganism, such as a bacterium, a fungus (including yeast), and a virus. Non-limiting examples of bacteria include Gram positive bacteria, such as *Actinomyces* (e.g., *A. meyeri* and *A. viscous*), *Bacillus* (e.g., *B. cereus, B. subtilis*), *Escherichia* (e.g., *E. coli*), *Staphylococcus* (e.g., *S. aureus*, including methicillin-resistant *S. aureus* (MRSA)), *Streptococcus* (e.g., *S. gordonii, S. mutans*); and Gram negative bacteria, such as *Aggregatibacter* (e.g., *A. actinomycetemocitans*), *Campylobacter* (e.g., *C. rectus*), *Eikenella* (e.g., *E. corrodens*), *Fusobacterium* (e.g., *F. nucleatum*), *Moraxella* (e.g., *M. catarrhalis*), *Porphyromonas* (e.g., *P. gingivalis*), *Prevotella* (e.g., *P. intermedia, P. melaninogenica, P. nigrescens*), *Pseudomonas* (e.g., *P. aeruginosa*), *Solobacterium*, (e.g., *S. moorei*), and *Viellonella* (e.g., *V. atypica, V. dispar*).

Non-limiting examples of fungus include yeast, such as *Candida* (e.g., *C. albicans*), *Capnocytophaga* (e.g., *C. gingivalis*), *Streptomyces* (e.g., *S. cervisiae*).

Non-limiting examples of viruses include influenza virus, coronavirus, coxsackievirus, foot-and-mouth virus, herpes virus (including herpes simplex virus (HSV)), mengovirus, nidovirus, parainfluenza virus, picornavirus, respiratory syncytial virus (RSV), and rhinovirus. In a particular embodiment, the virus is a rhinovirus.

As used herein, the term "microbial infection" is defined as the invasion and growth of a microbe on or in an individual's body where said microbe does not normally grow when the individual is healthy. Also encompassed by "microbial infection" is when the microbe grows to a greater degree on or in the body of an individual (e.g., the population of the microbe is larger) when compared to the microbe's population at the same body location when the individual is healthy.

As used herein, the term "individual" is defined as a subject which hosts the microbe. The individual is not particularly limited, and encompasses humans and non-human animals. Examples of non-human animals include domestic animals, such as dogs and cats; livestock/farm animals, such as horses, cows and pigs; and with exotic wildlife such as animals in zoos or in their natural environments.

As used herein, the term "inhibit," "inhibiting," or "inhibition" is defined as a reduction, amelioration, restraint, hindrance, hampering, slowing, deterrence, obstruction, constraint, delay, or postponement of a microbial infection.

II. Antimicrobial Compositions

The present disclosure relates to methods of inhibiting a microbial infection, reducing the number or occurrence of microbial infections suffered by a subject, or shortening the duration of a microbial infection comprising delivering into the oral cavity of the subject an oral composition comprising a first component comprising at least one Eh-raising compound and a second component comprising a zinc compound.

In any embodiment, methods to make compositions herein can be found in U.S. Pat. Nos. 6,409,992, 6,423,300 and 6,929,790 all to Kleinberg and each incorporated by reference in their entirety herein.

A. First Component

The first component of an oral composition disclosed herein may comprise one or more Eh-raising compounds. Non-limiting examples of Eh-raising compounds include oxidation reduction buffers; hydrogen peroxide; an oxyhalogen compound, such as sodium chlorite and sodium bromite; and commercially feasible combinations thereof. Additional examples of Eh-raising compounds include fermentable sugars, such as glucose, galactose, gulose, fructose, maltose, lactose and sucrose. Fermentable sugars, when metabolized by oral bacteria and in particular, oral streptococci, in the presence of oxygen, may produce, inter alia, hydrogen peroxide.

In particular embodiments, the Eh-raising compound can be an oxyhalogen compound, such as sodium chlorite or sodium bromite or a combination thereof.

In any embodiment, the concentration of the Eh-raising compound in the first component may range from about 0.01% (100 ppm) to about 3.0% (30,000 ppm), particularly about 0.04% (400 ppm) to about 1.2% (12,000 ppm), and more particularly about 0.06% (600 ppm) to about 0.6% (6,000 ppm). In particular embodiments, the concentration of the Eh-raising compound is about 0.01% (100 ppm) or about 0.02% (200 ppm) or about 0.03% (300 ppm) or about 0.04% (400 ppm) or about 0.05% (500 ppm) or about 0.06% (600 ppm) or about 0.07% (700 ppm) or about 0.08% (800 ppm) or about 0.09% (900 ppm) or about 0.1% (1000 ppm) or about 0.2% (2000 ppm) or about 0.3% (3000 ppm) or about 0.4% (4000 ppm) or about 0.5% (5000 ppm) or about 0.6% (6000 ppm) or about 0.7% (7000 ppm) or about 0.8% (8000 ppm) or about 0.9% (9000 ppm) or about 1.0% (10,000 ppm) by weight of the first component.

Additionally or alternatively, the concentration of the Eh-raising compound in the oral composition may range from about 0.005% (50 ppm) to about 1.5% (15,000 ppm), particularly about 0.02% (200 ppm) to about 0.6% (6,000 ppm), and more particularly about 0.03% (300 ppm) to about 0.3% (3,000 ppm) by weight of the oral composition.

Additionally or alternatively, the first component may further comprise a chlorine-containing compound. The chlorine-containing compound may be capable of inhibiting the catalase activity in the oral cavity. In a particular embodiment, a chlorine-containing compound can be added to the first component when the Eh-raising compound is hydrogen peroxide or a fermentable sugar in an amount sufficient to inhibit catalase(s) in the oral cavity from breaking down hydrogen peroxide or fermentable sugar. Suitable chlorine-containing compounds in the various oral compositions include, alkali metal chloride salts and alkaline earth metal chloride salts, such as, for example, NaCl and $CaCl_2$.

In any embodiment, the concentration of the chlorine-containing compound in the first component may range from about 0.5% (500 ppm) to about 2.5% (2500 ppm) by weight of the first component, particularly from about 0.7% (700 ppm) to about 2.3% (2300 ppm), and even more particularly from about 1.0% (1000 ppm) to about 2.0% (2000 ppm) by weight of the first component. In particular embodiments, the concentration of the chlorine-containing compound is about 1.0% (1000 ppm) or about 1.2% (1200 ppm) or about 1.4% (1400 ppm) or about 1.6% (1600 ppm) or about 1.8% (1800 ppm) or about 2.0% (2000 ppm) by weight of the first component.

Additionally or alternatively, the concentration of the chlorine-containing compound in the oral composition may range from about 0.25% (250 ppm) to about 1.25% (1250 ppm) by weight of the oral composition, particularly from about 0.35% (350 ppm) to about 1.15% (1150 ppm), and even more particularly from about 0.5% (500 ppm) to about 1.0% (1000 ppm) by weight of the oral composition.

B. Second Component

The second component of an oral composition disclosed herein may comprise one or more zinc compounds. Non-limiting examples of zinc compounds include any soluble zinc salt capable of providing freely available zinc ions when dissolved in water. For example, zinc chloride, zinc acetate, zinc lactate, zinc salicylate, zinc sulfate, zinc nitrate, and any possible combination thereof may be used. In a particular embodiment, the second component may comprise zinc chloride and an additional zinc compound. In a further particular embodiment, the zinc compound comprises zinc chloride.

In any embodiment, the concentration of zinc ion in the second component may range from about 0.02% (200 ppm) to about 1.0% (10000 ppm), more particularly about 0.04% (400 ppm) to about 0.7% (7000 ppm) by weight of the second component. In particular embodiments, the concentration of the zinc ion is about 0.04% (400 ppm) or about 0.05% (500 ppm) or about 0.06% (600 ppm) or about 0.07% (700 ppm) or about 0.08% (800 ppm) or about 0.09% (900 ppm) or about 0.1% (1000 ppm) or about 0.2% (2000 ppm) or about 0.3% (3000 ppm) or about 0.4% (4000 ppm) or about 0.5% (5000 ppm) or about 0.6% (6000 ppm) or about 0.7% (7000 ppm) by weight of the second component.

Additionally or alternatively, the concentration of the zinc ion in the oral composition may range from about 0.01% (100 ppm) to about 0.5% (5000 ppm), particularly from about 0.02% (200 ppm) to about 0.35% (3500 ppm) by weight of the oral composition.

Additionally or alternatively, the second component may also include CPC which has, among other things, antiviral, antibacterial, antifungal, anti-gingivitis and/or anti-plaque effects. CPC is a cationic surfactant having strong bactericidal and fungicidal effects. Particularly, CPC is a quaternary ammonium salt that conforms generally to the formula $C_{21}H_{38}NCl$. CPC can act primarily as an antimicrobial agent by penetrating the cell membrane, which causes leakage of components in the cell, disruption of bacterial and/or fungal metabolism, inhibition of cell growth, and finally cell death. CPC also is known to possess antiviral properties.

In any embodiment, the concentration of CPC in the second component may range from about 0.02% (200 ppm) to about 0.6% (6000 ppm), more particularly from about 0.09% (900 ppm) to about 0.2% (2000 ppm) by weight of the second component. In particular embodiments, the concentration of CPC is about 0.09% (900 ppm) or about 0.1% (1000 ppm) or about 0.2% (2000 ppm) by weight of the second component.

Additionally or alternatively, the concentration of CPC in the oral composition may range from about 0.01% (100 ppm) to about 0.3%, (3000 ppm), particularly from about 0.045% (450 ppm) to about 0.1% (1000 ppm) by weight of the oral composition. For example, in some embodiments, the concentration of CPC is about 0.05% (500 ppm) or about 0.06% (600 ppm) or about 0.07% (700 ppm) or about 0.08% (800 ppm) or about 0.09% (900 ppm) or about 0.1% (1000 ppm) by weight of the oral composition.

In particular embodiments, the second component may comprise about 0.02% (200 ppm) by weight to about 1.0% (10,000 ppm) by weight of zinc ion and about 0.02% (200 ppm) by weight to about 0.6% (6,000 ppm) by weight of CPC.

More particularly, the second component may comprise about 0.04% (400 ppm) by weight to about 0.7% (7000 ppm) by weight of zinc ion and about 0.09% (900 ppm) by weight to about 0.2% (2000 ppm) by weight of CPC.

C. Combination of First and Second Components

Any of the Eh-raising compounds listed above can be used in combination with any of the zinc compounds listed above. For example, any of the Eh-raising compounds listed above can be used in the first component, while any of the zinc compounds listed above can be used in the second component. There may be trace amounts of each in each component. For example, an oral composition is provided comprising:

a first component comprising at least one Eh-raising compound selected from the group consisting of an oxidation reduction buffer; hydrogen peroxide; an oxyhalogen compound, such as sodium chlorite and/or sodium bromite; and combinations thereof; and wherein the first component optionally contains at least one chlorine-containing compound selected from the group consisting of an alkali metal chloride salt and an alkaline earth metal chloride salt, such as NaCl and $CaCl_2$; and a second component comprising at least one zinc compound selected from the group consisting of zinc chloride; zinc acetate; zinc lactate; zinc salicylate; zinc sulfate; zinc nitrate; and combinations thereof; and optionally CPC.

In any embodiment, the oral composition may comprise a first component comprising hydrogen peroxide and optionally sodium chloride; and a second component comprising zinc chloride and optionally CPC.

In any embodiment, the oral composition may comprise a first component comprising a fermentable sugar and optionally sodium chloride, and a second component comprising zinc chloride and optionally CPC.

In any embodiment, the oral composition may comprise a first component comprising sodium chlorite and optionally sodium chloride; and a second component comprising zinc chloride and optionally CPC.

In any embodiment, the oral composition may comprise about 0.01% by weight to about 3.0% by weight of an Eh-raising compound; about 0.02% by weight to about 1.0% by weight of zinc ion; about 0.02% by weight to about 0.6% by weight of CPC; and at least one pharmaceutically acceptable carrier.

In any embodiment, the oral composition may comprise about 0.5% by weight to about 2.5% by weight of a chlorine-containing compound, and the second component may comprise about 0.02% by weight to about 1.0% by weight of zinc ion and about 0.02% by weight to about 0.6% by weight of CPC.

In any embodiment, an oral composition may comprise: about 0.005% by weight to about 1.5% by weight of an Eh-raising compound; about 0.01% by weight to about 0.5% by weight of zinc ion; and optionally about 0.01% by weight to about 0.3% by weight of CPC; and at least one pharmaceutically acceptable carrier, and the oral composition may be prepared by mixing a first component comprising the Eh-raising compound and a pharmaceutically acceptable carrier and a second component comprising a zinc compound, optionally CPC, and a pharmaceutically acceptable carrier.

D. Additional Components

An oral composition provided herein may also include additional components such as, for example, at least one of essential oils; a desensitizing agent; a whitening agent; an additional antimicrobial agent; an additional antibiotic; an additional anti-fungal agent; an additional anti-viral agent; an anti-cavity agent; an anti-plaque agent; an anti-tartar agent; an antioxidant; an anti-inflammatory; a deodorizer; a polishing agent; a detergent; a film-forming agent; a mineralizer or remineralizer; an agent to reduce or alleviate dry mouth; a coloring agent; a humectant; a sweetener; and/or flavorings.

For example, in any embodiment an oral composition provided herein may comprise: a first component comprising at least one Eh-raising compound; a second component comprising at least one zinc compound; a third component selected from the group consisting of essential oils; a whitening agent; cetylpyridinium chloride; an anti-microbial agent, such as; an anti-fungal agent; an anti-viral agent; an antioxident agent; an anti-cavity agent; an anti-plaque agent; a desensitizing agent; and an agent to alleviate or reduce dry mouth; and a pharmaceutically acceptable carrier.

In any embodiment, the oral composition may further comprise essential oils. For example, essential oils may comprise eucalyptol, menthol, methyl salicylate, and thymol.

In any embodiment, the oral composition may further comprise a desensitizing agent. Suitable desensitizing agents for use in the oral composition include, for example, benzocaine, potassium nitrate; potassium fluoride; strontium chloride; potassium chloride; potassium citrate; iron oxalate; sodium nitrate; lithium nitrate; magnesium nitrate; calcium nitrate; calcium hydroxide; dibasic calcium phosphate; strontium acetate; sodium monofluorophosphate; bisabolol; a local or systemic analgesic agent such as NSAIDS, aspirin, acetaminophen and/or codeine; and combinations thereof.

In any embodiment, the oral composition may further comprise a whitening agent. Suitable whitening agents for use in the oral composition include, for example, peroxides, pH-raising agents, sodium hypochlorite and salts thereof, and combinations thereof. For example, urea peroxide or carbamide peroxide, hydrogen peroxide, sodium bicarbonate, and combinations thereof.

In any embodiment, the oral composition may further comprise an anti-microbial agent in addition to or in replacement of CPC. Suitable anti-microbial agents for use in the oral composition include, for example, chlorhexidine; an anti-bacterial Gram-positive aerobic agent; an anti-bacterial Gram-negative agent; bromochloroprene; 1,6-bis(p-chlorophenyl diguanido) hexane, and water-soluble salts thereof, such as digluconate, diacetate, dilactate, dichlorohydrate; 1,6-di-(2-ethylhexyl diguanido) hexane and 1,6-di-(2-ethylhexyl diguanido) hexetidine, and water-soluble salts thereof; 1,6-di-(2-benzyl diguanido) hexane, 1,6-di-(2-benzyldiguanido) hexamidine, p-chlorophenyl diguanide, N-(4-chlorobenzyl)-N5-(2,4-dichlorobenzyl) oliguanide, and water-soluble salts thereof such as biguanide; betanapthol; chlorothymol; thymol; anethole; eucalyptol; carvacrol; menthol; phenol; amylphenol; hexylphenol; heptylphenol; octylphenol; hexylresorcinol; hexachlorophene [2,2-methylene bis(3,4,6-trichlorophenol)]; 1,1'-hexamethylene bis(5-)-p-chlorophenyl) bigauanide); methyl salicylate, and salts thereof; quaternary ammonium salt compounds such as morpholinium tetradecylsulfate, laurylpyridinium chloride, myristylpyridinium chloride, cetylpyridinium fluoride, cetylpyridinium chloride, cetylpyridinium bromide, cetylpyridinium iodide, stearylpyridinium chloride, dodecyltrimethylammonium chloride, tetradecyltrimethylammonium chloride, hexadecyltrimethylammonium bromide, C12-C16 benzyldimethylammonium chloride (benzethonium chloride), phenoxyethyldodecyldimethylammonium bromide (domiphen bromide); triclobisonium chloride; benzoic acid; sodium benzoate; potassium benzoate boric acid; tyrothricin; gramicidin; triclosan; mutanase; dextranase; stannous fluoride; and combinations thereof.

In any embodiment, the oral composition may further comprise additional anti-microbials such as antibiotic agents and/or anti-fungal agents. Suitable antibiotic and/or anti-fungal agents for use in the oral composition include, for example, amoxicillin, amoxicillin-clavulanate, clindamycin, doxycycline, metronidazole, metronidazole-spiramycin, and combinations thereof.

In any embodiment, the oral composition may further comprise an additional anti-viral agent. Suitable anti-viral agents for use in the oral composition include, for example, abacavir, aciclovir, acyclovir, adefovir dipivoxil, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, entry inhibitors, famciclovir, a fixed dose combination (anti-retroviral), fomivirsen, fosamprenavir, foscarnet, fosfonet, a fusion inhibitor, ganciclovir, ibacitabine, imunovir, idoxuridine, imiquimod, indinavir, inosine, integrase inhibitor, interferon type III, interferon type II, interferon type I, interferon, lamivudine, lopinavir, loviride, maraviroc, morozydine, methisazone, nelfinavir, nevirapine, nexavir, nucleoside analogues (nucleoside-analog reverse transcriptase inhibitors), oseltamivir, peginterferon alfa-2a, pegylated interferon alfa, penciclovir, peramivir, pleconaril, podofilox, podophyllotoxin, protease inhibitor, pyramidine, raltegravir, a reverse transcriptase inhibitor, ribavirin, rimantadine, ritonavir, saquinavir, stavudine, a synergistic enhancer (anti-retroviral), tea tree oil, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

In any embodiment, the oral composition may further comprise an anti-cavity agent. Suitable anti-cavity agents for use in the oral composition include, for example, fluoride, sodium fluoride, sodium monoflourophosphate, nicomethanol fluorhydrate, stannous fluoride, ammonium fluoride, potassium fluoride, aluminum fluoride, calcium fluoride, cuprous fluoride, barium fluoride; organic fluorides such as long-chain amine fluorides, fluorophosphates, aluminum difluorophosphate, sodium fluorozirconate, potassium fluorozirconate, tin fluorozirconate, sodium silicofluoride, fluorinated sodium calcium pyrophosphate, green tea, spirulina algae, and combinations thereof.

In any embodiment, the oral composition may further comprise an anti-plaque agent. Suitable anti-plaque agents for use in the oral composition include, for example, an alcohol such as ethanol, triclosan, sanguinarine, hexetidyne, zinc citrate, a fluoride, sodium lauryl sulfate, zinc phosphate, zinc acetate, zinc aspartate, zinc acetylmethionate, zinc citrate trihydrate, zinc tannate, zinc gluconate, zinc lactobionate, zinc maltobionate, zinc hydrolyzed collagen, zinc pyrrolidone carboxylic acid, zinc tribromosalicylanfiide, zinc caprylate, zinc octoate, zinc laurate, zinc myristate, zinc stearate, zinc oleate, zinc carbonate, zinc borate, zinc silicate, zinc sulfide, zinc sulfate, zinc oxide, zinc phenol sulfonate, zinc stannate, zinc dl-lactate, trihydrate, tannic acid, citric acid, acetic acid, lactic acid, sodium trihydrogen pyrophosphate, disodium dihydrogen pyrophosphate, trisodium hydrogen pyrophosphate, trisodium hydrogen pyrophosphate monohydrate, trisodium hydrogen pyrophosphate nonahydrate, tetrasodium pyrophosphate, tetrasodium pyrophosphate decahydrate, potassium trihydrogen pyrophosphate, dipotassium dihydrogen pyrophosphate, tripotassium hydrogen pyrophosphate, tetrapotassium pyrophosphate, diammonium dihydrogen pyrophosphate, triammonium hydrogen pyrophosphate, triammonium hydrogen pyrophosphate monohydrate, calcium dihydrogen pyrophosphate, calcium pyrophosphate, tetraaluminium pyrophosphate, and combinations thereof.

In any embodiment, the oral composition may further comprise an anti-tartar/anti-calculus agent. Suitable anti-tartar/anti-calculus agents for use in the oral composition include, for example, pyrophosphate, a zinc salt, and combinations thereof.

In any embodiment, the oral composition may further comprise an antioxidant. Suitable antioxidants for use in the oral composition include, for example, vitamins, such as vitamin A, C, or E; polyphenols; tocopherols; ethylenediaminetetracetic acid; butylated hydroxytoluene (BHT); and propyl gallate.

In any embodiment, the oral composition may further comprise an anti-inflammatory agent. Suitable anti-inflammatory agents for the gums include, but are not limited to, beta-glycerhetinic acid, enoxolone, salicylic acid, azulene, *Ginkgo biloba*, witch hazel, corticosteroids, NSAIDs, and salts thereof.

In any embodiment, the oral composition may further comprise an agent to reduce and/or alleviate dry mouth. Suitable agents to reduce and/or alleviate dry mouth include, but are not limited to cellulose gum, lactoferrin, lysozyme, lactoperoxidase, immunoglobulins, colustrum extract, glucose oxidase, amylase, amyloglucosidase, glucoxidase, papain, peptizyme, aloe vera, a nature-identical flavoring component that can make the mouth water and combinations thereof.

In any embodiment, the oral composition may further comprise a deodorizer. Suitable deodorizers for use in the oral composition include, for example, chlorhexidine, hydrogen peroxide, vitamin B, vitamin C, sodium bicarbonate, an herb, and combinations thereof.

In any embodiment, the oral composition may further comprise a polishing agent. Suitable polishing agents for use in the oral composition include, for example, calcium carbonate, dicalcium phosphate dihydrate, aluminum hydroxide, dental grade silicas, sodium carbonate, sodium bicarbonate, potassium carbonate, potassium bicarbonate, anhydrous calcium phosphate, dicalcium phosphate, tribasic calcium phosphate, sodium phosphate, potassium phosphate, calcium pyrophosphate, insoluble sodium metaphosphate, disodium orthophosphate, dibasic sodium phosphate, magnesium hydroxide, magnesium carbonate, magnesium silicate, magnesium trisilicate, trimagnesium phosphate, monomagnesium phosphate, magnesium oxide, stannic oxide, zinc oxide, bentonite, flour of pumice, α-alumina trihydrate, alumina, aluminum silicate, zirconium silicate, hydroxyapatite, crosslinked urea-formaldehyde resin, crosslinked melamine-formaldehyde resin, polymethacrylate, polymethylmethacrylate, polystyrene, powdered polyethylene, silica gel, dehydrated silica gel, sodium glycerophosphate, sodium trimetaphosphate, organic phosphates, and combinations thereof.

In any embodiment, the oral composition may further comprise a detergent. Suitable detergents for use in the oral composition include, for example, sodium lauryl sulphate, sodium lauryl sarcosinate, sodium methyl cocoyl taurate, polysorbates, sorbitan derivatives and combinations thereof.

In any embodiment, the oral composition may further comprise a film-forming agent. Suitable film-forming agents to protect against tar from tobacco and other tannins, include, but are not limited to, polyethylene glycol (PEG), petrolatum, liquid paraffin, dimethicone, magnesium stearate and stearic acid.

In any embodiment, the oral composition may further comprise a mineralizer or remineralizers. Suitable mineralizers or remineralizers of dental enamel include, but are not limited to, calcium in any form of mineral and organic apatite and hydroxyapatite salts.

In any embodiment, the oral composition may further comprise a coloring agent. Suitable coloring agents include, but are not limited to, red, blue and green food coloring, such as FD and C-type dyes and lakes, for example D&C blue #1, D&C blue #4, D&C brown #1, D&C green #5 through #8, D&C orange #4 through #11, D&C yellow #2 through #11, D&C red #6 through #40, FD&C blue #1, FD&C blue #2, FD&C blue #4, FD&C red #3, FD&C red #4, FD&C red #33, FD&C red #40, FD&C yellow #5, FD&C yellow #6, FD&C yellow #10, FD&C orange #4, FD&C green #3, carmine, and fruit and vegetable extracts.

In any embodiment, the oral composition may further comprise a humectant. Suitable humectants for use in oral composition include, but are not limited to, glycerin, propylene glycol, hydrogenated glucose syrup, polyethylene glycol-14 (PEG-14), polyethylene glycol-18 (PEG-18), polyethylene glycol-55 (PEG-55), polyethylene glycol-100 (PEG-100), polyethylene glycol-135 (PEG-135), polyethylene glycol-180 (PEG-180), polyethylene glycol-200 (PEG-4), polyethylene glycol-240 (PEG-240), polyethylene glycol-300 (PEG-6), polyethylene glycol-400 (PEG-8), polyethylene glycol-450 (PEG-9), polyethylene glycol-500 (PEG-10), polyethylene glycol-600 (PEG-12), polyethylene glycol-1540 (PEG-32), polyethylene glycol-2000 (PEG-40 or PEG-2M), polyethylene glycol-3000 (PEG-60), polyethylene glycol-4000 (PEG-75), polyethylene glycol-6000 (PEG-150), polyethylene glycol-9000 (PEG-9M or PEG-200), polyethylene glycol-20,000 (PEG-20M or PEG-350), polyethylene glycol-600,000 (PEG-14M), propylene glycol (PG), glycerol (glycerin), erythritol, xylitol, sorbitol, mannitol, lactitol, hydrogenated starch hydrolyzates.

In any embodiment, the oral composition may further comprise a sweetener that both improves the taste of the oral composition and freshens breath. Suitable sweeteners for use in the oral composition include, for example, xylitol, sodium saccharin, menthol, eucalyptus, sorbitol, mannitol, saccharin, aspartame, acesulfame potassium (acesulfame K), stevia, peppermint oil, spearmint oil, and combinations thereof.

In any embodiment, the oral composition may further comprise a flavoring agent. Suitable flavoring agents include, but are not limited to, menthol, eucalyptol, peppermint oil, spearmint oil, anise oil, benzaldehyde, bitter almond oil, camphor, cedar leaf oil, cinnamic aldehyde, cinnamon oil, citronella oil, clove oil, heliotropin, lavender oil, phenyl salicylate, pin oil, pin needle oil, rosemary oil, *sassafras* oil, thyme oil, thymol, wintergreen oil, lemon oil, orange oil, vanillin, carvone, anethole, irone, orris, carraway, coriander, pimento, eugenol, nutmeg and other flavoring oils generally regarded as safe (GRAS) by the Federal Drug and Food Administration (FDA).

In any embodiment, each of the first and second components may further comprise one or more pharmaceutically acceptable carriers. Pharmaceutically acceptable carriers for use in oral compositions and systems are well known in the art. Non-limiting examples of suitable pharmaceutically acceptable carriers include glycerin, water, saline, dextrose, sucrose, glycerol, polyethylene glycol, ethanol, sorbitol, mannitol, xylitol, and combinations thereof.

In any embodiment, the oral composition may comprise any combination of the above-described components, for example, any combination of the above-described desensitizing agents; whitening agents; additional anti-microbial agents; additional antibiotics; additional anti-fungal agents; additional anti-viral agents; anti-cavity agents; anti-plaque agents; anti-tartar agents; antioxidants; anti-inflammatories; an agent to reduce or alleviate dry mouth; a deodorizer; a polishing agent; a detergent; a film-forming agent; a mineralizer or remineralizer; a coloring agent; a humectant; a sweetener; and/or flavorings.

In any embodiment, the oral composition may comprise a first component comprising at least one Eh-raising compound; a second component comprising at least one zinc compound; and at least one additional component selected from the group consisting of essential oils; a whitening agent, cetylpyridinium chloride or an additional anti-microbial agent, an additional anti-fungal agent, and an additional anti-viral agent; an antioxident agent; an anti-cavity agent; an anti-plaque agent; a desensitizing agent and an agent to alleviate or reduce dry mouth; and a pharmaceutically acceptable carrier.

In particular embodiments, the first component may comprise sodium chlorite or hydrogen peroxide; the second component may comprise a zinc compound selected from the group consisting of zinc chloride, zinc acetate, zinc salicylate, zinc sulfate, and zinc nitrate; and optionally cetylpyridinium chloride; and an additional component selected from the group consisting of essential oils and a whitening agent may be present either as part of the first component, the second component, both the first and the second components, or as a separate third component.

An effective amount of such combinations is determined by the particular components utilized in the oral composition. Moreover, the oral composition is not limited to the agents and components described above, but may include various other agents and components.

The additional components disclosed in this section may be included in the first component, the second component, or in both components, of the present oral composition.

E. pH

The pH of an oral composition provided herein may depend upon the particular Eh-raising compound and the particular zinc compound combination used. For example, when the Eh-raising compound is hydrogen peroxide, the pH of the oral composition may range from about 3.0 to about 6.0. In one embodiment, the pH may range from about 3.5 to about 5.0, and in particular, from about 4.2 to about 4.8. This is because zinc ions, above a pH of about 6.0, combine with hydroxide ions in solution to form poorly soluble zinc hydroxide, thereby making freely available zinc ions less available.

Additionally or alternatively, the Eh-raising compound may be an oxyhalogen compound, such as sodium chlorite, and the pH of the first composition during storage may be between about 7.0 and about 8.5. The instability of zinc ions at a pH of 6.0 and above, and the instability of chlorite at a pH of about 6.0 and below, may make it advantageous at times to keep the first and the second compositions separate in two compartments or a two-phase system until ready for use.

In any embodiment, an oral composition may comprise a first component comprising about 0.04% by weight to about 1.2% by weight of sodium chlorite and the pH of the first component may range from about 7.0 to about 8.5, and a second component may comprise about 0.04% by weight to about 0.7% by weight of zinc ion and about 0.09% by weight to about 0.2% by weight of CPC and the pH of the second component may range from about 3.0 to about 6.0.

F. Xylitol

Additionally or alternatively, an oral composition provided herein may contain xylitol. The inclusion of xylitol can be used to facilitate decreasing periodontal disease and plaque adhesion within the oral cavity. Bacteria in the oral cavity release toxins that break down tissues, thereby facilitating the growth of infections. Specifically, bacteria assist in the creation of plaque along the gum line. Over time, continued exposure to plaque may lead to periodontal disease. Furthermore, dextrans in the oral cavity have been shown to accelerate the aggregation of bacteria, such as adhesions of plaque to teeth are increased. Xylitol facilitates reducing the formation of dextrans in the oral cavity. As such, plaque adhesion is reduced, which leads to a reduction in periodontal disease.

Furthermore, xylitol use has shown a reduction in new tooth decay, along with arrest and even reversal of existing dental caries. Specifically, xylitol may suppress at least some of the most harmful strains of oral bacteria, such that the use of xylitol may provide a long-lasting change in bacterial communities present in the oral cavity. Moreover, xylitol has the ability to enhance the mineralization of the enamel on teeth and may be used to effectively treat small decay spots on teeth. Additionally, xylitol may stimulate saliva flow and help keep salivary minerals in a useful form. As such, xylitol may be utilized to increase saliva production for people suffering a dry mouth due to illness, aging, or drug side effects.

In any embodiment, xylitol may be mixed with a small amount of titanium tetrafluoride to provide an enhanced effect that further reduces plaque adhesion in the oral cavity.

Furthermore, a xylitol-containing oral composition provided herein may also be useful to reduce microbes that may cause ear, nose, and/or throat infections. Furthermore, a xylitol-containing oral composition may also be useful in reversing bone loss, decreasing insulin resistance, decreasing hypertension which can be associated with diabetes, and/or correcting hormonal imbalances.

Typically, the amount of xylitol in an oral composition provided herein will depend on the type of oral composition and the desired function of the xylitol. For example, when the oral composition is a mouth rinse, the composition may include an amount of xylitol of about 0.1% by weight to about 15% by weight of the total oral composition. In another embodiment, when the oral composition is a confectionary or a chewing gum, the oral composition may include an amount of xylitol from about 0.1% by weight to about 50% by weight. Xylitol can be included in the first or second component. Alternatively, the xylitol may be stored separately from each of the first and second component.

In any embodiment, an oral composition provided herein optionally contains xylitol and/or other components as described herein. For example, in any embodiment, an oral composition formed may include a concentration of xylitol ranging from about 0.1% to about 50% by weight of the oral composition. In particular embodiments, the concentration of xylitol may range from about 0.1% to about 50% by weight of the oral composition.

IV. Methods of Use

Methods are provided herein for inhibiting a microbial infection comprising delivering an oral composition as described herein to the oral cavity of a subject. The microbial infection may be a bacterial infection, fungal infection, and/or a viral infection.

Additionally or alternatively, methods for reducing the occurrence or number of microbial infections in a subject comprising delivering an oral composition as described herein to the oral cavity of a subject are also provided herein. The reduction of microbial infections can be measured over a given unit of time. For example, the number of microbial infections is reduced over the span of about 3 months, about 4 months, about 5 months, about 6 months, about 7 months, about 8 months, about 9 months, about 10 months, about 11 months, about one year or about two years.

Additionally or alternatively, methods for shortening the duration of a microbial infection comprising delivering an oral composition as described herein to the oral cavity of a subject are also provided herein. For example, the duration of a cold may be shortened by about 2 weeks, about one week, about 6 days, about 5 days, about 4 days, about 3 days, about 2 days or about 1 day.

Additionally or alternatively, methods for treating, alleviating or preventing or reducing the occurrence of cold sores, such as those caused by the herpes virus, in a subject comprising delivering an oral composition as described herein to the oral cavity of a subject are also provided herein.

Additionally or alternatively, methods for preventing or alleviating dental diseases, such as those caused by a microbial infection, are provided herein comprising delivering into the oral cavity effective amounts of an Eh-raising compound, a zinc ion, and optionally CPC, wherein the dental diseases include, for example, gingivitis, periodontitis, and tooth decay. Without being bound by theory, it is believed that an effective amount of an Eh-raising compound, a zinc ion, and/or CPC may be an amount sufficient to raise the oxidation-reduction potential of the oral cavity to normal levels. In any embodiment, the tooth decay, gingivitis, and/or periodontitis may be reduced. For example, an effective amount of an oral composition may be an amount sufficient to inhibit a microbial infection, such as the growth of harmful Gram-negative anaerobic bacteria which may cause gingivitis and periodontitis.

As noted above, the microbial infection may be a bacterial infection, fungal infection, and/or a viral infection. In any embodiment, the viral infection may be caused by a rhinovirus, influenza virus, parainfluenza virus, coronavirus, respiratory syncytial virus (RSV), poliovirus, picornavirus, foot-and-mouth disease virus, mengovirus, or herpes virus. In particular embodiments, the viral infection may be caused by a rhinovirus.

Additionally or alternatively, the microbial infection may be a bacterial infection. In any embodiment, the bacterial infection may be caused by Gram positive bacteria, such as *Actinomyces* (e.g., *A. meyeri* and *A. viscous*), *Bacillus* (e.g., *B. cereus, B. subtilis*), *Escherichia* (e.g., *E. coli*), *Staphylococcus* (e.g., *S. aureus*, including methicillin-resistant *S. aureus* (MRSA)), *Streptococcus* (e.g., *S. gordonii, S. mutans*); and Gram negative bacteria, such as *Aggregatibacter* (e.g., *A. actinomycetemocitans*), *Campylobacter* (e.g., *C. rectus*), *Eikenella* (e.g., *E. corrodens*), *Fusobacterium* (e.g., *F. nucleatum*), *Moraxella* (e.g., *M. catarrhalis*), *Porphyromonas* (e.g., *P. gingivalis*), *Prevotella* (e.g., *P. intermedia, P. melaninogenica, P. nigrescens*), *Pseudomonas* (e.g., *P. aeruginosa*), *Solobacterium*, (e.g., *S. moorei*), and *Viellonella* (e.g., *V. atypica, V. dispar*).

Additionally or alternatively, the microbial infection may be a fungal infection. In any embodiment, the microbial infection may be caused by *Candida* (e.g., *C. albicans*), *Capnocytophaga* (e.g., *C. gingivalis*), or *Streptomyces* (e.g., *S. cervisiae*).

In any embodiment, the oral composition may be prepared by mixing a first component comprising the Eh-raising compound and a pharmaceutically acceptable carrier and a second component comprising the zinc compound, optionally CPC, and a pharmaceutically acceptable carrier. In particular embodiments, the first and the second components are both solutions.

In any embodiment, the first and second components of the oral composition are mixed prior to delivery to the oral cavity of the subject. For example, the first and second components may be mixed within 10 minutes, within 5 minutes, within 2 minutes, within 1 minute, within 30 seconds, or immediately prior to delivery to the oral cavity.

In any embodiment, an oral composition provided herein may be delivered in a volume appropriate to rinse the oral cavity of the subject. For example, an oral composition may be delivered in a volume from about 5 to about 50 mL. In a further example, the oral composition may be delivered in a volume of about 5 mL, about 10 mL, about 15 mL, about 20 mL, about 25 mL, about 30 mL, about 35 mL or about 40 mL.

In any embodiment, an oral composition provided herein may be delivered to the oral cavity of a subject from one to five times per day, such as one, two, three, four, or five times per day. In particular embodiments, an oral composition provided herein may be delivered three times per day, two times per day, or once per day.

In any embodiment, an oral composition provided herein may be delivered to the oral cavity of a subject at the first sign of symptoms of infection and for any given number of days thereafter, for example, about 20 days, about 15 days, or about 10 days from the first sign of symptoms of infection.

A. Delivery Forms

The oral compositions described herein may be provided in a variety of oral vehicles proper for delivery to humans and/or non-human animals. For example, in any embodiment, the oral composition may take the form of a solid, liquid, spray, gel, foam, syrup, or powder. In any embodiment, the oral composition may be orally delivered through an oral care product, a food product, a tablet, a capsule, a flash-melt formulation, a candy, a lozenge, a chewing gum, a confection, a toothpaste, a mouth rinse, a breath spray and/or a mint. In particular embodiments, the oral composition is in the form of a mouth rinse.

Additionally or alternatively, the oral composition may be a solution where one of the first or the second components is encapsulated (or any equivalent to a capsule). For example, the first component can be a solution and the second component can be present in the solution in an encapsulated form. Alternatively, the second component can be a solution and the first component can be present in the solution in an encapsulated form.

In particular embodiments, both the first and second components of the oral composition are independent solutions.

Additionally or alternatively, the oral composition may be a tablet, confectionary or a chewing gum where the first and second components are substantially prevented from contacting each other until brought into contact by for example, the user. Further examples include a two-phase tablet or capsule that can be used wherein the first component and the second component are substantially prevented from mixing or coming into contact with each other.

Additionally or alternatively, the oral composition may be delivered to non-human animals in the form of a water additive, a pet mouth wash or rinse, toothpaste, pet spray, pet treat, pet food, animal feed, and/or a chew toy.

V. Systems/Kits

The oral compositions provided herein comprise a first component and a second component, as described herein, which are stored separately. As used herein, the phrase "stored separately" refers to substantially preventing a first component and a second component from contacting each other until desired, such as at the time and location of use. The term "substantially prevent" is intended to encompass both complete physical separation of the first and second components from each other until the desired time and location of use, and where the first and second components may come into inconsequential chemical contact. "Inconsequential chemical contact" is contact which does not alter the chemical or antimicrobial properties of either component, alone or together. Any known container or device for storing components separately can be used to store the composition of the present disclosure. The first and second components may be stored in separate containers. Alternatively, the first and second components may be stored in the same container having separate compartments for each component. In particular embodiments, a first and second component can be contained in separate containers such as two bottles, tubes, capsules, or equivalent container, to substantially prevent premature contact. Alternatively, a syringe-like barrel can be used where the components are kept separate until the plunger is activated. In any embodiment, the first and second components can be in a single bottle comprising two mutually exclusive compartments which separate the two components until use.

The first and second components are stored separately or substantially prevented from contact with each other, and may be brought into contact, such as by mixing with each other, by users at the time and location of use. The components may be brought into contact about 10 seconds to about 30 minutes before use. In particular embodiments, the first and the second components are brought into contact with each other about 10 minutes prior to use, and more particularly, within about 5 minutes prior to use.

In any embodiment, the first and second components may be provided in a system and/or kit which forms an oral composition comprising both components at the time and location of use as described in more detail below. The system may facilitate inhibiting microbial infections, reducing the number of microbial infections in an individual, shortening the duration of a microbial infection, and/or preventing the reduction of an oxidation-reduction potential (Eh) of the oral cavity and, at the same time, may facilitate increasing the existing oxidation-reduction potential to a level, wherein an oral environment is created that is not conducive to microbial infection. In particular embodiments, the system and/or kit may comprise two bottles, each containing the first or second component, respectfully. Alternatively, the system and/or kit may comprise a single bottle which comprises separate compartments for the first and second components.

The systems and/or kits described herein may further include one or more dosage cups/containers for delivery of the proper amount of the oral composition.

Additionally or alternatively, the systems and/or kits may comprise written information, such as indications and instructions for use as well as a list of active and inactive ingredients. Packaging, such as a box, may also be included in the systems and/or kits.

VI. Articles of Manufacture and Packaging

The present disclosure also provides an article of manufacture comprising a packaging material and one or more of the oral compositions described herein contained within the packaging material. The packaging material used to contain the oral compositions can comprise glass, plastic, metal or any other suitably inert material. For example, a dentifrice containing the oral composition may be contained in a collapsible tube, such as aluminum, or plastic, or a squeeze, pump, or pressurized dispenser for measuring out the contents or in a tearable sachet. Furthermore, the packaging material can be capable of retaining the zinc compound and the Eh-raising compound separately, such that they can be mixed prior to use of the oral composition. Moreover, any of the above-described optional components or combinations thereof may be premixed with any of the first and second components, or the cetylpyridinium chloride. Alternatively, any of the above-described optional components or combinations thereof may be stored separately from the first and second components. As such, an optional compound, the zinc compound, and the Eh-raising compound can all be mixed prior to use of the oral composition.

Separate compositions can optionally be co-packaged, for example in a single container or in a plurality of containers. For example, separate containers for the zinc compound and Eh-raising compound utilized. The separate containers can also be presented to a consumer separately and independently, for use according to methods described herein.

VII. Further Embodiments

The invention can additionally or alternatively include one or more of the following embodiments.

Embodiment 1

A method for inhibiting a microbial infection, the method comprising delivering into the oral cavity of a subject an oral composition comprising a first component comprising at least one Eh-raising compound and a second component comprising a zinc compound, wherein the concentration of the Eh-raising compound ranges from about 0.1% to about 3.0% (w/v) and wherein the concentration of the zinc compound ranges from about 0.02% to about 0.2% (w/v).

Embodiment 2

A method for reducing the number of microbial infections suffered by an individual, the method comprising delivering into the oral cavity of a subject an oral composition comprising a first component comprising at least one Eh-raising compound and a second component comprising a zinc compound, wherein the concentration of the Eh-raising compound ranges from about 0.1% to about 3.0% (w/v) and wherein the concentration of the zinc compound ranges from about 0.02% to about 0.2% (w/v).

Embodiment 3

A method for shortening the duration of a microbial infection, the method comprising delivering into the oral cavity of a subject an oral composition comprising a first component comprising at least one Eh-raising compound and a second component comprising a zinc compound, wherein the concentration of the Eh-raising compound ranges from about 0.1% to about 3.0% (w/v) and wherein the concentration of the zinc compound ranges from about 0.02% to about 0.2% (w/v).

Embodiment 4

The method of any one of Embodiments 1-3, wherein the microbial infection is a selected from the group consisting of a bacterial infection and a viral infection.

Embodiment 5

The method of Embodiment 4, wherein the microbial infection is a viral infection.

Embodiment 6

The method of Embodiment 5, wherein the viral infection is caused by a virus selected from the group consisting of rhinovirus, influenza virus, parainfluenza virus, coronavirus, respiratory syncytial virus (RSV), poliovirus, picornavirus, foot-and-mouth disease virus, mengovirus, and herpes virus.

Embodiment 7

The method of Embodiment 6, wherein the viral infection is caused by a rhinovirus.

Embodiment 8

The method of any one of Embodiments 1-7, wherein the first component and second component are stored separately from each other.

Embodiment 9

The method of Embodiment 8, wherein either one or both of the first and second components are solutions.

Embodiment 10

The method of Embodiments 8 or 9, wherein the first component and second component are mixed no more than about 5 minutes prior to delivery to the oral cavity.

Embodiment 11

The method of any one of Embodiments 1-10, wherein the second component further comprises cetylpyridinium chloride (CPC) in a concentration ranging from about 0.02% to about 0.6% (w/v).

Embodiment 12

The method of any one of Embodiments 1-11, wherein the second component contains a freely available zinc ion concentration from about 0.04% to about 0.12% (w/v).

Embodiment 13

The method of any one of Embodiments 1-12, wherein the zinc compound in the second component is selected from the group consisting of zinc chloride, zinc sulfate, zinc acetate, zinc lactate, zinc salicylate, and zinc nitrate.

Embodiment 14

The method of any one of Embodiments 1-13, wherein the Eh-raising compound in the first component ranges from about 0.1% to about 1.0% (w/v).

Embodiment 15

The method of any one of Embodiments 1-14, wherein the Eh-raising compound in the first component is selected from the group consisting of hydrogen peroxide and an oxyhalogen compound.

Embodiment 16

The method of any one of Embodiments 1-15, wherein the Eh-raising compound in the first component is an oxyhalogen compound and the zinc compound in the second component is zinc chloride.

Embodiment 17

The method of any one of Embodiment 16, wherein the oxyhalogen compound in the first component is sodium chlorite or sodium bromite.

Embodiment 18

The method of any one of Embodiment 17, wherein the sodium chlorite or sodium bromite in the first component is stored in a medium having a pH from about 7.0 to about 8.5, and the zinc compound in the second component is stored in a medium having a pH from about 3.0 to about 6.0.

Embodiment 19

The method of any one of Embodiments 1-18, wherein the oxyhalogen compound is sodium chlorite.

Embodiment 20

The method of any one of Embodiments 1-19, wherein the oral composition is an oral care product, a food product, a lozenge, a chewing gum, or a confection.

Embodiment 21

The method of Embodiment 2, wherein the reduction in the number of microbial infections is over the course of one year.

Examples

Oral compositions in accordance with the present disclosure are formulated for various evaluations. For all formulations, the pH range of Solution 1 is from about 7.0 to about 7.65; and the pH range of Solution 2 is from about 4.2 to about 4.8. The compositions below are disclosed as mg of ingredient per liter of total composition.

Example 1

| | | Formulation 1 | |
|---|---|---|---|
| Solution 1 | water | 982620 (mg/L) | 98.26% |
| | benzoate buffer | 16005 | 1.60% |
| | sodium chlorite | 1375 | 0.14% |
| Solution 2 | water | 833440 | 83.34% |
| | glycerin | 120000 | 12.00% |
| | inactive ingredients | 38760 | 3.88% |
| | benzoate buffer | 2600 | 0.26% |
| | zinc chloride | 5200 | 0.52% |

Example 2

| | Formulation 2 | | |
|---|---|---|---|
| Solution 1 | water | 982620 (mg/L) | 98.26% |
| | benzoate buffer | 12030 | 1.20% |
| | sodium chlorite | 5350 | 0.54% |
| Solution 2 | water | 845440 | 84.54% |
| | glycerin | 112000 | 11.20% |
| | inactive ingredients | 38760 | 3.88% |
| | benzoate buffer | 2500 | 0.25% |
| | zinc chloride | 1300 | 0.13% |

Example 3

| | Formulation 3 | | |
|---|---|---|---|
| Solution 1 | water | 982620 (mg/L) | 98.26% |
| | benzoate buffer | 16695 | 1.67% |
| | sodium chlorite | 685 | 0.07% |
| Solution 2 | water | 838640 | 83.86% |
| | glycerin | 114000 | 11.40% |
| | inactive ingredients | 38760 | 3.88% |
| | benzoate buffer | 2700 | 0.27% |
| | zinc chloride | 5900 | 0.59% |

Example 4

| | Formulation 4 | | |
|---|---|---|---|
| Solution 1 | water | 982620 (mg/L) | 98.26% |
| | benzoate buffer | 14420 | 1.44% |
| | sodium chlorite | 2960 | 0.30% |
| Solution 2 | water | 826740 | 82.67% |
| | glycerin | 128000 | 12.80% |
| | inactive ingredients | 38760 | 3.88% |
| | benzoate buffer | 2800 | 0.28% |
| | zinc chloride | 3700 | 0.37% |

Example 5

| | Formulation 5 | | |
|---|---|---|---|
| Solution 1 | water | 982620 (mg/L) | 98.26% |
| | benzoate buffer | 14080 | 1.41% |
| | sodium chlorite | 3300 | 0.33% |
| Solution 2 | water | 829340 | 82.93% |
| | glycerin | 126000 | 12.60% |
| | inactive ingredients | 38760 | 3.88% |
| | benzoate buffer | 2900 | 0.29% |
| | zinc chloride | 3000 | 0.30% |

Example 6

| | Formulation 6 | | |
|---|---|---|---|
| Solution 1 | water | 982620 (mg/L) | 98.26% |
| | benzoate buffer | 12655 | 1.27% |
| | sodium chlorite | 4725 | 0.47% |
| Solution 2 | water | 840840 | 84.08% |
| | glycerin | 115000 | 11.50% |
| | inactive ingredients | 38760 | 3.88% |
| | benzoate buffer | 3000 | 0.30% |
| | zinc chloride | 2400 | 0.24% |

Example 7

| | Formulation 7 | | |
|---|---|---|---|
| Solution 1 | water | 982620 (mg/L) | 98.26% |
| | benzoate buffer | 13530 | 1.35% |
| | sodium chlorite | 3850 | 0.39% |
| Solution 2 | water | 845440 | 84.54% |
| | glycerin | 110000 | 11.00% |
| | inactive ingredients | 38760 | 3.88% |
| | benzoate buffer | 2500 | 0.25% |
| | zinc chloride | 3300 | 0.33% |

Example 8

| | Formulation 8 | | |
|---|---|---|---|
| Solution 1 | water | 982620 (mg/L) | 98.26% |
| | benzoate buffer | 13130 | 1.31% |
| | sodium chlorite | 4250 | 0.43% |
| Solution 2 | water | 826900 | 82.69% |
| | glycerin | 126500 | 12.65% |
| | inactive ingredients | 38800 | 3.88% |
| | benzoate buffer | 5000 | 0.50% |
| | zinc chloride | 2800 | 0.28% |

Example 9

| | Formulation 9 | | |
|---|---|---|---|
| Solution 1 | water | 982620 (mg/L) | 98.26% |
| | benzoate buffer | 14805 | 1.48% |
| | sodium chlorite | 2575 | 0.26% |
| Solution 2 | water | 845440 | 84.54% |
| | glycerin | 106500 | 10.65% |
| | inactive ingredients | 38800 | 3.88% |
| | benzoate buffer | 7360 | 0.74% |
| | zinc chloride | 1900 | 0.19% |

Example 10

| | Formulation 10 | | |
|---|---|---|---|
| Solution 1 | water | 982620 (mg/L) | 98.26% |
| | benzoate buffer | 15430 | 1.54% |
| | sodium chlorite | 1950 | 0.20% |
| Solution 2 | water | 834200 | 83.42% |
| | glycerin | 119000 | 11.90% |
| | inactive ingredients | 38800 | 3.88% |
| | benzoate buffer | 4000 | 0.40% |
| | zinc chloride | 4000 | 0.40% |

Example 11

Formulation 11

| | | | |
|---|---|---|---|
| Solution 1 | water | 982620 (mg/L) | 98.26% |
| | benzoate buffer | 16290 | 1.63% |
| | sodium chlorite | 1090 | 0.11% |
| Solution 2 | water | 845440 | 84.54% |
| | glycerin | 109000 | 10.90% |
| | inactive ingredients | 38800 | 3.88% |
| | benzoate buffer | 4760 | 0.48% |
| | zinc chloride | 2000 | 0.20% |

Example 12

Formulation 12

| | | | |
|---|---|---|---|
| Solution 1 | water | 982620 (mg/L) | 98.26% |
| | benzoate buffer | 11430 | 1.14% |
| | sodium chlorite | 5950 | 0.60% |
| Solution 2 | water | 845440 | 84.54% |
| | glycerin | 102500 | 10.25% |
| | inactive ingredients | 38800 | 3.88% |
| | benzoate buffer | 12460 | 1.25% |
| | zinc chloride | 800 | 0.08% |

Example 13

Formulation 13

| | | | |
|---|---|---|---|
| Solution 1 | water | 982620 (mg/L) | 98.262% |
| | benzoate buffer | 16005 | 1.60% |
| | sodium chlorite | 1375 | 0.1375% |
| Solution 2 | water | 831640 | 83.164% |
| | glycerin | 120000 | 12.000% |
| | inactive ingredients | 39560 | 3.956% |
| | benzoate buffer | 2600 | 0.260% |
| | zinc chloride | 5200 | 0.520% |
| | CPC | 1000 | 0.100% |

Example 14

Formulation 14

| | | | |
|---|---|---|---|
| Solution 1 | water | 982620 (mg/L) | 98.262% |
| | benzoate buffer | 12030 | 1.20% |
| | sodium chlorite | 5350 | 0.5350% |
| Solution 2 | water | 843640 | 84.364% |
| | glycerin | 112000 | 11.200% |
| | inactive ingredients | 39560 | 3.956% |
| | benzoate buffer | 2500 | 0.250% |
| | zinc chloride | 1300 | 0.130% |
| | CPC | 1000 | 0.100% |

Example 15

Formulation 15

| | | | |
|---|---|---|---|
| Solution 1 | water | 982620 (mg/L) | 98.262% |
| | benzoate buffer | 16695 | 1.67% |
| | sodium chlorite | 685 | 0.0685% |
| Solution 2 | water | 836840 | 83.684% |
| | glycerin | 114000 | 11.400% |
| | inactive ingredients | 39560 | 3.956% |
| | benzoate buffer | 2700 | 0.270% |
| | zinc chloride | 5900 | 0.590% |
| | CPC | 1000 | 0.100% |

Example 16

Formulation 16

| | | | |
|---|---|---|---|
| Solution 1 | water | 982620 (mg/L) | 98.262% |
| | benzoate buffer | 14420 | 1.44% |
| | sodium chlorite | 2960 | 0.2960% |
| Solution 2 | water | 824940 | 82.494% |
| | glycerin | 128000 | 12.800% |
| | inactive ingredients | 39560 | 3.956% |
| | benzoate buffer | 2800 | 0.280% |
| | zinc chloride | 3700 | 0.370% |
| | CPC | 1000 | 0.100% |

Example 17

Formulation 17

| | | | |
|---|---|---|---|
| Solution 1 | water | 982620 (mg/L) | 98.262% |
| | benzoate buffer | 14080 | 1.41% |
| | sodium chlorite | 3300 | 0.3300% |
| Solution 2 | water | 827540 | 82.754% |
| | glycerin | 126000 | 12.600% |
| | inactive ingredients | 39560 | 3.956% |
| | benzoate buffer | 2900 | 0.290% |
| | zinc chloride | 3000 | 0.300% |
| | CPC | 1000 | 0.100% |

Example 18

Formulation 18

| | | | |
|---|---|---|---|
| Solution 1 | water | 982620 (mg/L) | 98.262% |
| | benzoate buffer | 12655 | 1.27% |
| | sodium chlorite | 4725 | 0.4725% |
| Solution 2 | water | 839040 | 83.904% |
| | glycerin | 115000 | 11.500% |
| | inactive ingredients | 39560 | 3.956% |
| | benzoate buffer | 3000 | 0.300% |
| | zinc chloride | 2400 | 0.240% |
| | CPC | 1000 | 0.100% |

Example 19

Formulation 19

| | | | |
|---|---|---|---|
| Solution 1 | water | 982620 (mg/L) | 98.262% |
| | benzoate buffer | 13530 | 1.353% |
| | sodium chlorite | 3850 | 0.3850% |

Formulation 19 (continued)

| | | | |
|---|---|---|---|
| Solution 2 | water | 843640 | 84.364% |
| | glycerin | 110000 | 11.00% |
| | inactive ingredients | 39560 | 3.956% |
| | benzoate buffer | 2500 | 0.25% |
| | zinc chloride | 3300 | 0.33% |
| | CPC | 1000 | 0.10% |

Example 20

Formulation 20

| | | | |
|---|---|---|---|
| Solution 1 | water | 982620 (mg/L) | 98.2620% |
| | benzoate buffer | 13130 | 1.313% |
| | sodium chlorite | 4250 | 0.425% |
| Solution 2 | water | 825100 | 82.51% |
| | glycerin | 126500 | 12.65% |
| | inactive ingredients | 39600 | 3.96% |
| | benzoate buffer | 5000 | 0.50% |
| | zinc chloride | 2800 | 0.28% |
| | CPC | 1000 | 0.10% |

Example 21

Formulation 21

| | | | |
|---|---|---|---|
| Solution 1 | water | 982620 (mg/L) | 98.2620% |
| | benzoate buffer | 14805 | 1.481% |
| | sodium chlorite | 2575 | 0.258% |
| Solution 2 | water | 843640 | 84.36% |
| | glycerin | 106500 | 10.65% |
| | inactive ingredients | 39600 | 3.96% |
| | benzoate buffer | 7360 | 0.74% |
| | zinc chloride | 1900 | 0.19% |
| | CPC | 1000 | 0.10% |

Example 22

Formulation 22

| | | | |
|---|---|---|---|
| Solution 1 | water | 982620 (mg/L) | 98.2620% |
| | benzoate buffer | 15430 | 1.543% |
| | sodium chlorite | 1950 | 0.195% |
| Solution 2 | water | 832400 | 84.364% |
| | glycerin | 119000 | 11.90% |
| | inactive ingredients | 39600 | 3.96% |
| | benzoate buffer | 4000 | 0.40% |
| | zinc chloride | 4000 | 0.40% |
| | CPC | 1000 | 0.10% |

Example 23

Formulation 23

| | | | |
|---|---|---|---|
| Solution 1 | water | 982620 (mg/L) | 98.2620% |
| | benzoate buffer | 16290 | 1.6290% |
| | sodium chlorite | 1090 | 0.1090% |
| Solution 2 | water | 843640 | 84.364% |
| | glycerin | 109000 | 10.90% |
| | inactive ingredients | 39600 | 3.96% |
| | benzoate buffer | 4760 | 0.48% |
| | zinc chloride | 2000 | 0.20% |
| | CPC | 1000 | 0.10% |

Example 24

Formulation 24

| | | | |
|---|---|---|---|
| Solution 1 | water | 982620 (mg/L) | 98.2620% |
| | benzoate buffer | 11430 | 1.143% |
| | sodium chlorite | 5950 | 0.595% |
| Solution 2 | water | 843640 | 84.364% |
| | glycerin | 102500 | 10.25% |
| | inactive ingredients | 39600 | 3.96% |
| | benzoate buffer | 12460 | 1.25% |
| | zinc chloride | 800 | 0.08% |
| | CPC | 1000 | 0.10% |

Example 25

Formulation 25

| | | | |
|---|---|---|---|
| Solution 1 | water | 984004 (mg/L) | 98.40% |
| | benzoate buffer | 13121 | 1.31% |
| | sodium chlorite | 1375 | 0.14% |
| | CMC | 1500 | 0.15% |
| Solution 2 | water | 769240 | 76.93% |
| | glycerin | 100000 | 10.00% |
| | Sorbitol | 100000 | 10.00% |
| | inactive ingredients | 20660 | 2.06% |
| | benzoate buffer | 2600 | 0.26% |
| | zinc chloride | 5200 | 0.52% |
| | CMC | 2300 | 0.23% |

Example 26

Formulation 26

| | | | |
|---|---|---|---|
| Solution 1 | water | 984004 (mg/L) | 98.40% |
| | benzoate buffer | 9046 | 0.90% |
| | sodium chlorite | 5350 | 0.54% |
| | CMC | 1600 | 0.16% |
| Solution 2 | water | 793040 | 79.31% |
| | glycerin | 85000 | 8.50% |
| | Sorbitol | 95000 | 9.50% |
| | inactive ingredients | 20660 | 2.06% |
| | benzoate buffer | 2500 | 0.25% |
| | zinc chloride | 1300 | 0.13% |
| | CMC | 2500 | 0.25% |

Example 27

Formulation 27

| | | | |
|---|---|---|---|
| Solution 1 | water | 984004 (mg/L) | 98.40% |
| | benzoate buffer | 13611 | 1.36% |
| | sodium chlorite | 685 | 0.07% |
| | CMC | 1700 | 0.17% |

Formulation 27

| | | | |
|---|---|---|---|
| Solution 2 | water | 788540 | 78.85% |
| | glycerin | 90000 | 9.00% |
| | Sorbitol | 90000 | 9.00% |
| | inactive ingredients | 20560 | 2.06% |
| | benzoate buffer | 2600 | 0.26% |
| | zinc chloride | 5900 | 0.59% |
| | CMC | 2400 | 0.24% |

Example 28

Formulation 28

| | | | |
|---|---|---|---|
| Solution 1 | water | 984004 (mg/L) | 98.40% |
| | benzoate buffer | 11236 | 1.12% |
| | sodium chlorite | 2960 | 0.30% |
| | CMC | 1800 | 0.18% |
| Solution 2 | water | 790740 | 79.07% |
| | glycerin | 95000 | 9.50% |
| | Sorbitol | 85000 | 8.50% |
| | inactive ingredients | 20560 | 2.06% |
| | benzoate buffer | 2700 | 0.27% |
| | zinc chloride | 3700 | 0.37% |
| | CMC | 2300 | 0.23% |

Example 29

Formulation 29

| | | | |
|---|---|---|---|
| Solution 1 | water | 984004 (mg/L) | 98.40% |
| | benzoate buffer | 10796 | 1.08% |
| | sodium chlorite | 3300 | 0.33% |
| | CMC | 1900 | 0.19% |
| Solution 2 | water | 791440 | 79.14% |
| | glycerin | 115000 | 11.50% |
| | Sorbitol | 65000 | 6.50% |
| | inactive ingredients | 20560 | 2.06% |
| | benzoate buffer | 2800 | 0.28% |
| | zinc chloride | 3000 | 0.30% |
| | CMC | 2200 | 0.22% |

Example 30

Formulation 30

| | | | |
|---|---|---|---|
| Solution 1 | water | 984004 (mg/L) | 98.40% |
| | benzoate buffer | 9271 | 0.93% |
| | sodium chlorite | 4725 | 0.47% |
| | CMC | 2000 | 0.20% |
| Solution 2 | water | 791900 | 79.19% |
| | glycerin | 105000 | 10.50% |
| | Sorbitol | 75000 | 7.50% |
| | inactive ingredients | 20600 | 2.06% |
| | benzoate buffer | 3000 | 0.30% |
| | zinc chloride | 2400 | 0.24% |
| | CMC | 2100 | 0.21% |

Example 31

Formulation 31

| | | | |
|---|---|---|---|
| Solution 1 | water | 984004 (mg/L) | 98.40% |
| | benzoate buffer | 10144 | 1.01% |
| | sodium chlorite | 3852 | 0.39% |
| | CMC | 2000 | 0.20% |
| Solution 2 | water | 791918 | 79.19% |
| | glycerin | 100000 | 10.00% |
| | Sorbitol | 80000 | 8.00% |
| | inactive ingredients | 20587 | 2.06% |
| | benzoate buffer | 2495 | 0.25% |
| | zinc chloride | 3000 | 0.30% |
| | CMC | 2000 | 0.20% |

Example 32

Formulation 32

| | | | |
|---|---|---|---|
| Solution 1 | water | 984004 (mg/L) | 98.40% |
| | benzoate buffer | 9746 | 0.96% |
| | sodium chlorite | 4250 | 0.43% |
| | CMC | 2000 | 0.21% |
| Solution 2 | water | 789660 | 78.97% |
| | glycerin | 104000 | 10.40% |
| | Sorbitol | 76000 | 7.60% |
| | inactive ingredients | 20640 | 2.06% |
| | benzoate buffer | 5000 | 0.50% |
| | zinc chloride | 2800 | 0.28% |
| | CMC | 1900 | 0.19% |

Example 33

Formulation 33

| | | | |
|---|---|---|---|
| Solution 1 | water | 984004 (mg/L) | 98.40% |
| | benzoate buffer | 11221 | 1.12% |
| | sodium chlorite | 2575 | 0.26% |
| | CMC | 2200 | 0.22% |
| Solution 2 | water | 788260 | 78.83% |
| | glycerin | 100000 | 10.00% |
| | Sorbitol | 80000 | 8.00% |
| | inactive ingredients | 20640 | 2.06% |
| | benzoate buffer | 7400 | 0.74% |
| | zinc chloride | 1900 | 0.19% |
| | CMC | 1800 | 0.18% |

Example 34

Formulation 34

| | | | |
|---|---|---|---|
| Solution 1 | water | 984004 (mg/L) | 98.40% |
| | benzoate buffer | 11746 | 1.17% |
| | sodium chlorite | 1950 | 0.20% |
| | CMC | 2300 | 0.23% |
| Solution 2 | water | 789400 | 78.94% |
| | glycerin | 92000 | 9.20% |
| | Sorbitol | 88000 | 8.80% |
| | inactive ingredients | 20600 | 2.06% |
| | benzoate buffer | 4000 | 0.40% |
| | zinc chloride | 4000 | 0.40% |
| | CMC | 2000 | 0.20% |

Example 35

| | Formulation 35 | | |
|---|---|---|---|
| Solution 1 | water | 984004 (mg/L) | 98.40% |
| | benzoate buffer | 12506 | 1.25% |
| | sodium chlorite | 1090 | 0.11% |
| | CMC | 2400 | 0.24% |
| Solution 2 | water | 790860 | 79.09% |
| | glycerin | 97500 | 9.75% |
| | Sorbitol | 82500 | 8.25% |
| | inactive ingredients | 20640 | 2.06% |
| | benzoate buffer | 4800 | 0.48% |
| | zinc chloride | 2000 | 0.20% |
| | CMC | 1700 | 0.17% |

Example 36

| | Formulation 36 | | |
|---|---|---|---|
| Solution 1 | water | 984004 (mg/L) | 98.40% |
| | benzoate buffer | 7546 | 0.75% |
| | sodium chlorite | 5950 | 0.60% |
| | CMC | 2500 | 0.25% |
| Solution 2 | water | 784500 | 78.45% |
| | glycerin | 110000 | 11.00% |
| | Sorbitol | 70000 | 7.00% |
| | inactive ingredients | 20600 | 2.06% |
| | benzoate buffer | 12500 | 1.25% |
| | zinc chloride | 800 | 0.08% |
| | CMC | 1600 | 0.16% |

Example 37: Acceleration and Occurrence Reduction of the Common Cold Study

Overview

SmartMouth® Advanced Cold Rinse is a rinse designed for the acceleration and/or occurrence reduction of the common cold. All ingredients found in SmartMouth® Cold Rinse are identified by the Food and Drug Administration (FDA) as Generally Recognized as Safe (GRAS). Example 7 formulation was used in this study.

Objectives

The aim of this study is to provide evidence on the clinical efficacy of SmartMouth® Advanced Cold Rinse for the acceleration and/or occurrence reduction of the common cold.

Study Population

A 12 week trial was conducted on 47 subjects divided into two groups. Group 1 consisted of subjects #37-47 in FIGS. 1-4 that focus on cold acceleration. Group 2 consisted of subjects #1-36 in FIGS. 1-4 that focused on occurrence reduction of the common cold.

Research Design and Methods

Visit 1

Subjects signed the informed consent, non-disclosure agreement, medical screening questionnaire, and dental screening questionnaire. All participants were informed of the nature of the study, its purpose, and any possible risks. Subjects were also informed as to the length of the study and the specific procedures that were carried out. Subjects were informed that this is a voluntary study and that they are free to withdraw from the study at any time.

Subjects electing to move forward with the study were assigned a group:

Group 1—Subject received one (1)—32 oz. unit of SmartMouth® Advanced Cold Rinse and written directions instructing the subject to rinse three times per day at the first sign of the common cold for 10 days.

Group 2—Subject received one (1)—32 oz unit of SmartMouth® Advanced Cold Rinse and written directions instructing the subject to use the rinse two times per day (After brushing once in the morning and one before bed).

Visit 2

Group 1—Subject returned 4 weeks after visit 1 and received one (1)—32 oz. unit of SmartMouth® Advanced Cold Rinse and written directions instructing the subject to rinse three time per day at the first sign of the common cold for 10 days.

Group 2—Subject returned 4 weeks after visit 1 and will receive one (1)—32 oz unit of SmartMouth® Advanced Cold Rinse and written directions instructing the subject to use the rinse two times per day (After brushing once in the morning and one before bed).

Visit 3

Group 1—Subject returned 4 weeks after visit 2 and received one (1)—32 oz. unit of SmartMouth® Advanced Cold Rinse and written directions instructing the subject to rinse three time per day at the first sign of the common cold for 10 days.

Group 2—Subject returned 4 weeks after visit 2 and received one (1)—32 oz unit of SmartMouth® Advanced Cold Rinse and written directions instructing the subject to use the rinse two times per day (After brushing once in the morning and one before bed).

Visit 4

Group 1—Subject returned 4 weeks after visit 3 and received one (1)—32 oz. unit of SmartMouth® Advanced Cold Rinse and written directions instructing the subject to rinse three time per day at the first sign of the common cold for 10 days.

Group 2—Subject returned 4 weeks after visit 3 and received one (1)—32 oz unit of SmartMouth® Advanced Cold Rinse and written directions instructing the subject to use the rinse two times per day (After brushing once in the morning and one before bed).

Data Evaluation

Measurement Reliability:

Group 1: Subjects reported the number of times symptoms of the common cold arose and the duration time the symptoms remained during the 12 week period.

Group 2: Subjects reported the number of colds during the 12 week period.

Statistical Analyses:

According to the Center for Disease Control and Prevention the average American adults have an average of 2-3 colds per year and recover within 7-10 days. Data from the subjects will be collected and measured against the standard set by the CDC.

Results:

The results from the study for visits 2, 3, 4 and 5 are provided in FIGS. 1-4 respectively. Forty-seven (47) subjects were studied. The number of colds, durations and weights of the solution 1 (S1) and solution 2 (S2) bottles were measured when coming into each visit (S1 IN and S2 IN) and out of each visit (S1 OUT and S2 OUT). The results demonstrate that the compositions provided herein containing an Eh-raising agent and freely available zinc ion inhibit or reduce the occurrence or duration of the common cold.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. A method for reducing the duration of a rhinovirus infection suffered by a subject, the method comprising delivering an oral composition into an oral cavity of the subject, the oral composition comprising:
    a first component comprising about 0.1% to about 3.0% (w/v) of at least one $E_h$-raising compound, wherein the $E_h$-raising compound is sodium chlorite or sodium bromite; and
    a second component comprising about 0.02% to about 0.2% (w/v) of a zinc compound.

2. The method of claim 1, wherein the first component and the second component are stored separately from each other.

3. The method of claim 1, wherein either one or both of the first and second components are solutions.

4. The method of claim 2, wherein the first component and the second component are mixed no more than about 5 minutes prior to delivery into the oral cavity.

5. The method of claim 1, wherein the second component further comprises about 0.02% to about 0.6% (w/v) cetylpyridinium chloride (CPC).

6. The method of claim 1, wherein the second component contains a freely available zinc ion concentration from about 0.04% to about 0.12% (w/v).

7. The method of claim 1, wherein the zinc compound is selected from the group consisting of zinc chloride, zinc sulfate, zinc acetate, zinc lactate, zinc salicylate, and zinc nitrate.

8. The method of claim 1, wherein the $E_h$-raising compound ranges from about 0.1% to about 1.0% (w/v).

9. The method of claim 1, wherein the zinc compound in the second component is zinc chloride.

10. The method of claim 1, wherein the sodium chlorite or sodium bromite of the first component is stored in a medium having a pH from about 7.0 to about 8.5, and the zinc compound of the second component is stored in a medium having a pH from about 3.0 to about 6.0.

11. The method of claim 1, wherein the $E_h$-raising compound in the first component is sodium chlorite.

12. The method of claim 1, wherein the oral composition is an oral care product, a food product, or a confection.

* * * * *